US008771201B2

(12) United States Patent
Gabriel et al.

(10) Patent No.: US 8,771,201 B2
(45) Date of Patent: Jul. 8, 2014

(54) HEALTH MONITORING BOLUS

(75) Inventors: Karim M. Gabriel, Lunenburg, MA (US); James H. Rooney, III, Harvard, MA (US); Charles M. Ciany, Newport, RI (US); Robert L. Lescanec, Norwood, MA (US)

(73) Assignee: Vital Herd, Inc., Lunenberg, MA (US)

( * ) Notice: Subject to any disclaimer, the term of this patent is extended or adjusted under 35 U.S.C. 154(b) by 863 days.

(21) Appl. No.: 12/802,218

(22) Filed: Jun. 2, 2010

(65) Prior Publication Data
US 2011/0301437 A1    Dec. 8, 2011

(51) Int. Cl.
*A61B 5/00* (2006.01)
*A61F 2/02* (2006.01)
*B65D 81/00* (2006.01)
*A61B 5/103* (2006.01)
*A61B 5/117* (2006.01)

(52) U.S. Cl.
USPC .................. 600/582; 600/549; 600/593

(58) Field of Classification Search
USPC ......... 600/549, 593, 578, 573, 562, 582, 580, 600/300, 301, 302, 309, 109
See application file for complete search history.

(56) References Cited

U.S. PATENT DOCUMENTS

| | | | | |
|---|---|---|---|---|
| 4,239,040 A | * | 12/1980 | Hosoya et al. | 604/135 |
| 4,257,427 A | * | 3/1981 | Bucalo | 600/582 |
| 4,262,632 A | | 4/1981 | Hanton et al. | |
| 4,439,197 A | * | 3/1984 | Honda et al. | 604/891.1 |
| 4,481,952 A | * | 11/1984 | Pawelec | 600/582 |
| 5,170,801 A | * | 12/1992 | Casper et al. | 600/582 |
| 5,318,557 A | * | 6/1994 | Gross | 604/891.1 |
| 5,482,008 A | | 1/1996 | Stafford et al. | |
| 5,499,626 A | * | 3/1996 | Willham et al. | 600/300 |
| 5,604,531 A | * | 2/1997 | Iddan et al. | 348/76 |
| 5,697,384 A | * | 12/1997 | Miyawaki et al. | 128/899 |
| 5,697,684 A | | 12/1997 | Gyovai | |
| 5,833,603 A | * | 11/1998 | Kovacs et al. | 600/317 |
| 5,948,993 A | | 9/1999 | Ting et al. | |
| 5,963,132 A | * | 10/1999 | Yoakum | 340/572.1 |
| 5,971,942 A | * | 10/1999 | Gu et al. | 600/582 |
| 5,984,875 A | | 11/1999 | Brune | |
| 5,993,378 A | * | 11/1999 | Lemelson | 600/109 |
| 6,059,733 A | | 5/2000 | Brune et al. | |

(Continued)

FOREIGN PATENT DOCUMENTS

WO  WO 2005/081963 A2   9/2005
WO  WO 2005/112615 A1  12/2005

OTHER PUBLICATIONS

International Bureau, Patent Cooperation Treaty, "First Notice Informing the applicant of the communication of the international application (to designated offices which do not apply the 30 month time limit under Article 22(1), International Application No. PCT/US2007/021700", Sep. 24, 2008, 1 pg.
SmartBolus®, http://www.smartbolus.com, Nov. 4, 2009, 11 pgs.

(Continued)

*Primary Examiner* — Max Hindenburg
*Assistant Examiner* — May Abouelela
(74) *Attorney, Agent, or Firm* — Morrison & Foerster LLP

(57) ABSTRACT

A bolus for insertion in a body fluid includes a housing, a chamber in the housing admitting body fluid therein, and a transducer in the housing providing a signal through the body fluid for measuring the pH level and/or temperature of the body fluid. The transducer also generates a signal in response to vibrations to detecting one or more additional physiological parameters.

28 Claims, 20 Drawing Sheets

(56) References Cited

U.S. PATENT DOCUMENTS

| | | | |
|---|---|---|---|
| 6,099,482 A * | 8/2000 | Brune et al. | 600/549 |
| 6,202,596 B1 | 3/2001 | Lopez et al. | |
| 6,285,897 B1 | 9/2001 | Kilcoyne et al. | |
| 6,329,920 B1 | 12/2001 | Morrison et al. | |
| 6,371,927 B1 * | 4/2002 | Brune et al. | 600/549 |
| 6,474,263 B2 * | 11/2002 | Caja Lopez et al. | 119/174 |
| 6,527,729 B1 | 3/2003 | Turcott | |
| 6,535,131 B1 * | 3/2003 | Bar-Shalom et al. | 340/573.1 |
| 6,535,151 B2 | 3/2003 | Coene | |
| 6,632,175 B1 * | 10/2003 | Marshall | 600/309 |
| 6,664,897 B2 | 12/2003 | Pape et al. | |
| 6,689,056 B1 * | 2/2004 | Kilcoyne et al. | 600/300 |
| 6,694,161 B2 * | 2/2004 | Mehrotra | 600/361 |
| 7,004,910 B2 | 2/2006 | Lindsey | |
| 7,026,939 B2 * | 4/2006 | Letkomiller et al. | 340/572.7 |
| 7,026,941 B1 | 4/2006 | Anderson | |
| 7,062,308 B1 | 6/2006 | Jackson | |
| 7,076,284 B2 * | 7/2006 | Segawa et al. | 600/424 |
| 7,083,579 B2 * | 8/2006 | Yokoi et al. | 600/593 |
| 7,118,531 B2 * | 10/2006 | Krill | 600/309 |
| 7,350,481 B2 | 4/2008 | Bar-Shalom | |
| 7,427,265 B1 * | 9/2008 | Keilman et al. | 600/300 |
| 7,452,338 B2 * | 11/2008 | Taniguchi | 600/593 |
| 7,511,733 B2 * | 3/2009 | Takizawa et al. | 348/68 |
| 7,611,480 B2 * | 11/2009 | Levy | 604/27 |
| 7,634,305 B2 * | 12/2009 | Davidson et al. | 600/424 |
| 7,637,864 B2 * | 12/2009 | Yokoi et al. | 600/114 |
| 7,717,862 B2 * | 5/2010 | Stoltz | 600/582 |
| 7,857,767 B2 * | 12/2010 | Ferren et al. | 600/481 |
| 7,940,973 B2 * | 5/2011 | Lee et al. | 382/128 |
| 7,998,059 B2 * | 8/2011 | Fujimori | 600/109 |
| 8,016,756 B2 * | 9/2011 | Homan et al. | 600/302 |
| 8,068,897 B1 * | 11/2011 | Gazdzinski | 600/476 |
| 8,125,516 B2 * | 2/2012 | Iddan et al. | 348/76 |
| 8,142,350 B2 * | 3/2012 | Frisch et al. | 600/160 |
| 8,152,713 B2 * | 4/2012 | Fujimori | 600/109 |
| 8,187,174 B2 * | 5/2012 | Wang | 600/117 |
| 8,235,055 B2 * | 8/2012 | Mintchev et al. | 128/899 |
| 8,290,556 B2 * | 10/2012 | Rabinovitz et al. | 600/310 |
| 8,317,681 B1 * | 11/2012 | Gazdzinski | 600/118 |
| 8,333,754 B2 * | 12/2012 | Boyden et al. | 604/891.1 |
| 8,394,034 B2 * | 3/2013 | Iddan et al. | 600/582 |
| 8,406,490 B2 * | 3/2013 | Gat et al. | 382/128 |
| 8,439,822 B2 * | 5/2013 | Shigemori et al. | 600/103 |
| 8,444,554 B2 * | 5/2013 | Lewkowicz et al. | 600/160 |
| 8,636,648 B2 * | 1/2014 | Gazdzinski | 600/109 |
| 8,663,093 B2 * | 3/2014 | Rabinovitz et al. | 600/117 |
| 2001/0051766 A1 * | 12/2001 | Gazdzinski | 600/309 |
| 2002/0111544 A1 * | 8/2002 | Iddan | 600/310 |
| 2003/0005771 A1 * | 1/2003 | Percin et al. | 73/627 |
| 2003/0020810 A1 * | 1/2003 | Takizawa et al. | 348/68 |
| 2003/0023150 A1 * | 1/2003 | Yokoi et al. | 600/300 |
| 2003/0195400 A1 * | 10/2003 | Glukhovsky | 600/302 |
| 2003/0205208 A1 | 11/2003 | Bar-Shalom | |
| 2003/0216622 A1 * | 11/2003 | Meron et al. | 600/300 |
| 2004/0068204 A1 * | 4/2004 | Imran et al. | 600/593 |
| 2004/0073459 A1 | 4/2004 | Barthell | |
| 2004/0122315 A1 * | 6/2004 | Krill | 600/437 |
| 2004/0133131 A1 * | 7/2004 | Kuhn et al. | 600/593 |
| 2004/0162501 A1 * | 8/2004 | Imran | 600/547 |
| 2004/0181155 A1 * | 9/2004 | Glukhovsky | 600/476 |
| 2005/0177069 A1 * | 8/2005 | Takizawa et al. | 600/573 |
| 2005/0182342 A1 * | 8/2005 | Dinsmoor et al. | 600/593 |
| 2005/0192489 A1 * | 9/2005 | Marshall | 600/302 |
| 2005/0245794 A1 * | 11/2005 | Dinsmoor | 600/302 |
| 2005/0264412 A1 | 12/2005 | Levesque et al. | |
| 2006/0079740 A1 * | 4/2006 | Silver et al. | 600/309 |
| 2006/0155174 A1 * | 7/2006 | Glukhovsky et al. | 600/301 |
| 2006/0224063 A1 * | 10/2006 | Segawa et al. | 600/424 |
| 2006/0229592 A1 * | 10/2006 | Yokoi et al. | 606/1 |
| 2007/0053795 A1 * | 3/2007 | Laugharn et al. | 422/99 |
| 2007/0088194 A1 * | 4/2007 | Tahar et al. | 600/102 |
| 2007/0173738 A1 * | 7/2007 | Stoltz | 600/582 |
| 2008/0033257 A1 * | 2/2008 | Yokoi et al. | 600/300 |
| 2008/0114224 A1 * | 5/2008 | Bandy et al. | 600/302 |
| 2008/0161660 A1 * | 7/2008 | Arneson et al. | 600/302 |
| 2008/0208077 A1 * | 8/2008 | Iddan et al. | 600/582 |
| 2008/0287833 A1 * | 11/2008 | Semler et al. | 600/593 |
| 2008/0294023 A1 * | 11/2008 | Rabinovitz et al. | 600/309 |
| 2008/0306360 A1 * | 12/2008 | Robertson et al. | 600/302 |
| 2009/0005639 A1 * | 1/2009 | Kawano et al. | 600/109 |
| 2009/0005727 A1 * | 1/2009 | Hood et al. | 604/65 |
| 2009/0012372 A1 * | 1/2009 | Burnett et al. | 600/300 |
| 2009/0030293 A1 * | 1/2009 | Cooper et al. | 600/302 |
| 2009/0030294 A1 * | 1/2009 | Petisce et al. | 600/302 |
| 2009/0124871 A1 * | 5/2009 | Arshak et al. | 600/302 |
| 2009/0137883 A1 * | 5/2009 | Chiba et al. | 600/302 |
| 2009/0182207 A1 * | 7/2009 | Riskey et al. | 600/302 |
| 2009/0187392 A1 * | 7/2009 | Riskey et al. | 703/11 |
| 2010/0170446 A1 * | 7/2010 | Manneke et al. | 119/14.02 |
| 2010/0305415 A1 * | 12/2010 | Rabinovitz et al. | 600/302 |
| 2011/0046458 A1 * | 2/2011 | Pinedo et al. | 600/309 |
| 2011/0092787 A1 * | 4/2011 | Bulitta et al. | 600/364 |
| 2011/0196255 A1 * | 8/2011 | Kassab | 600/549 |
| 2011/0306897 A1 * | 12/2011 | Imran | 600/547 |
| 2012/0035434 A1 * | 2/2012 | Ferren et al. | 600/301 |
| 2012/0310054 A1 * | 12/2012 | Birk | 600/302 |
| 2013/0060101 A1 * | 3/2013 | Takizawa et al. | 600/302 |
| 2013/0172690 A1 * | 7/2013 | Arne et al. | 600/301 |

OTHER PUBLICATIONS

K-State professors working on sensor-based system to monitor livestock herds, http://www.k-state.edu/media/webzine/safetyandsecurity/livestockmonitor.html, Jan. 26, 2009, 2 pgs.

Forbes.com—Magazine Article, Entrepreneurs, "Outstanding in His Field", http://members.forbes.com/forbes/2007/0618/088_print.html, Aug. 1, 2007, 2 pgs.

Smith et al., "An Integrated Cattle Health Monitoring System", Proc. 28th IEEE, EMBS Annual International Conference, NYC, USA, Aug. 30-Sep. 3, 2006, pp. 4659-4662.

Popovich et al., "Information Technology in the Age of Emergency Public Health Response", IEEE Engineering in Medicine and Biology, Sep./Oct. 2002, pp. 48-55.

International Searching Authority, Written Opinion, PCT/IL2005/000515, Aug. 19, 2005, 5 pgs. (unnumbered).

International Searching Authority, International Search Report and Written Opinion, PCT/US2007/021700, Sep. 23, 2008, 12 pgs. (unnumbered).

* cited by examiner

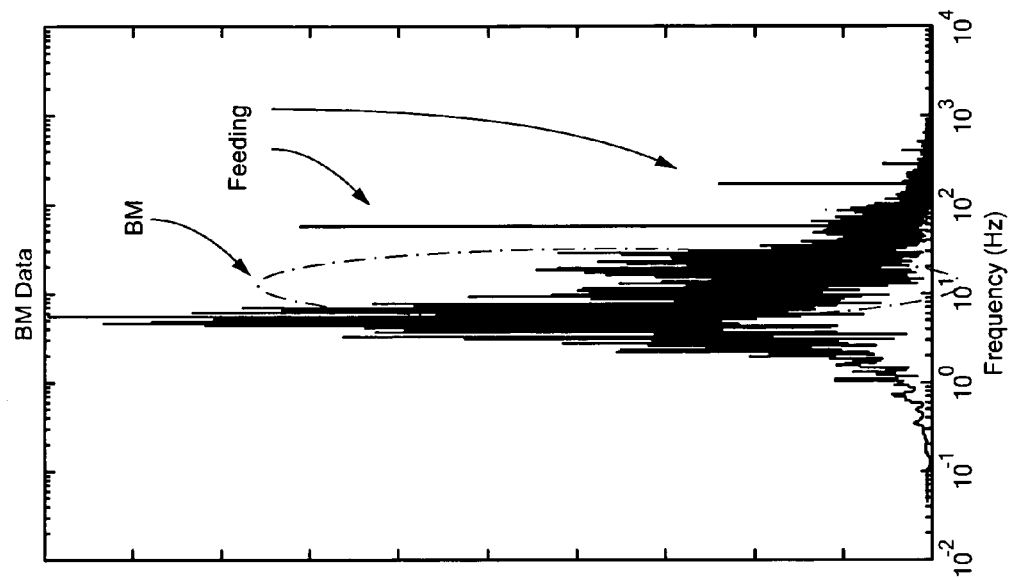
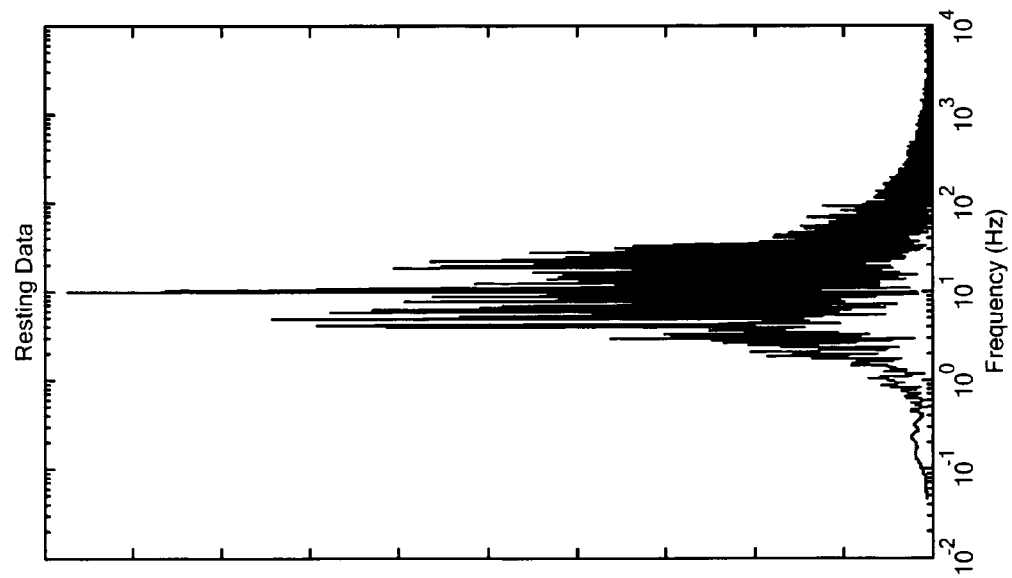

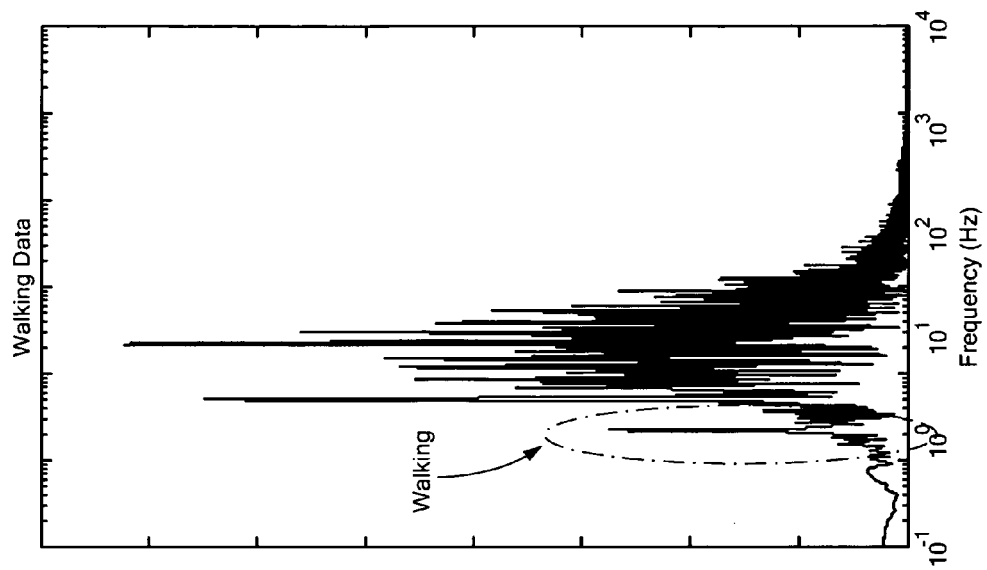
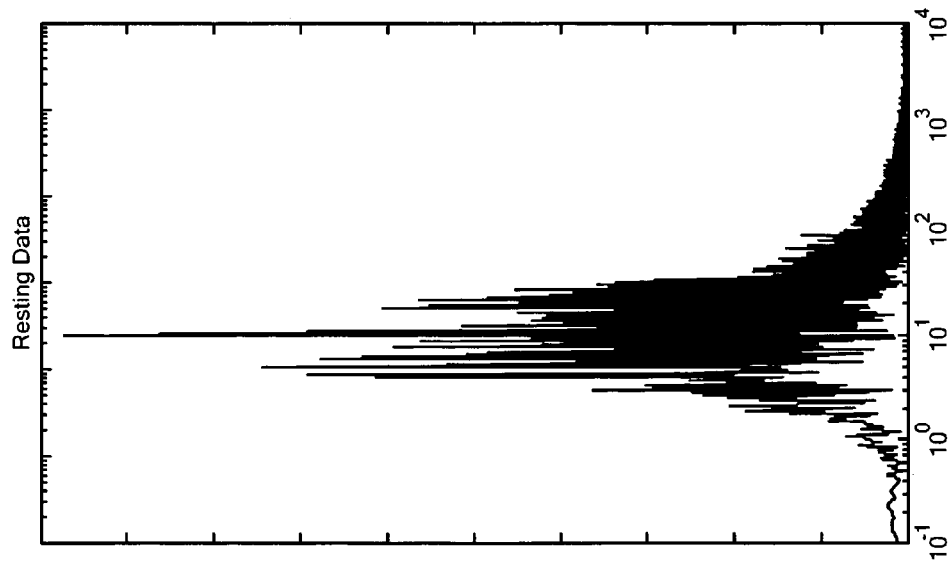

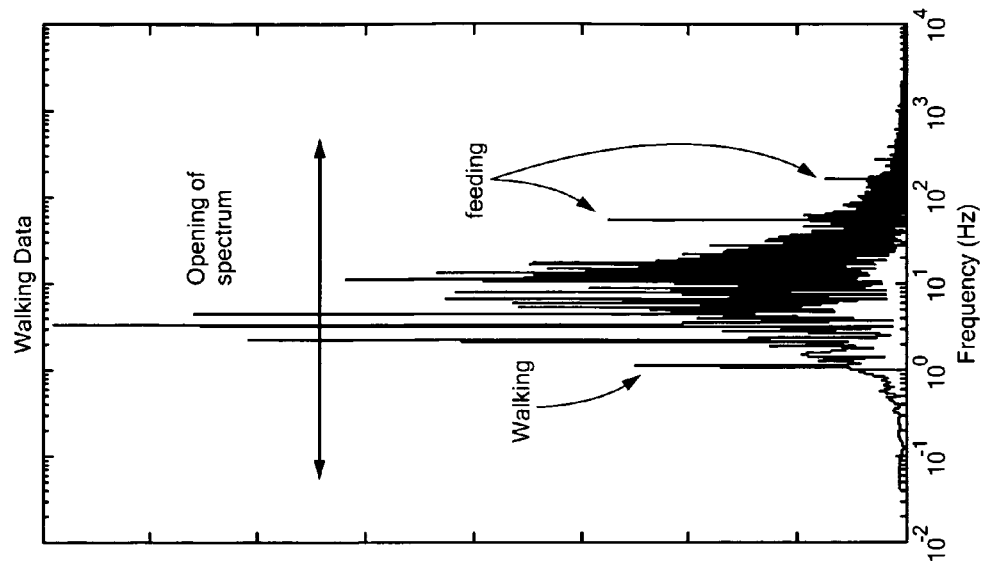
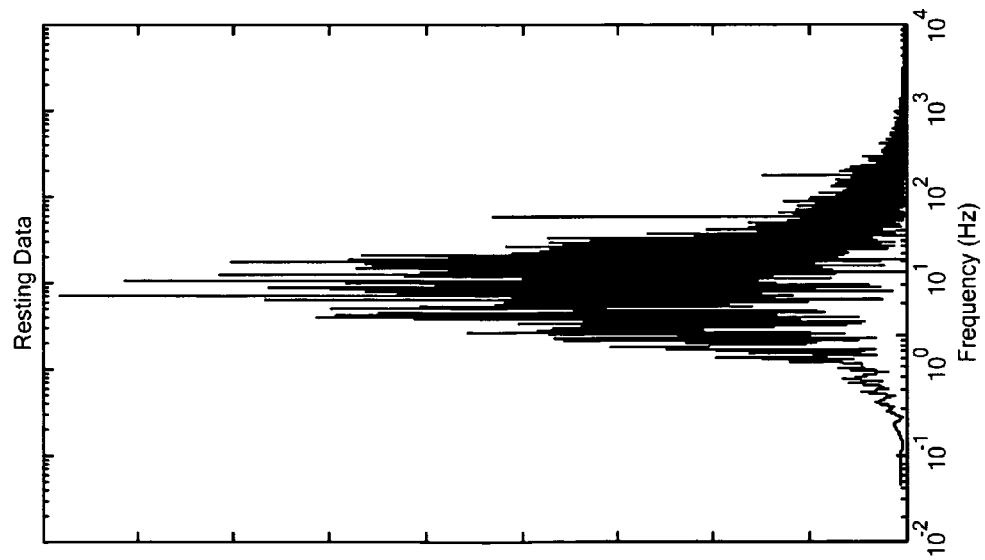
FIG. 24B
FIG. 24A

HEALTH MONITORING BOLUS

FIELD OF THE INVENTION

The subject invention relates to devices used to monitor the health of subjects such as cows.

BACKGROUND OF THE INVENTION

An electronic bolus is a device inserted into a subject in order to monitor one or more parameters typically indicative of the health and condition of the subject and provide a means of unique identification. Various forms of electronic boluses have been proposed in the art. Most include several sensors while some only provide identification. Others include only one specific sensor and are limited in the amount of information that can be ascertained. Some have sensors disposed on the outside of the bolus. Examples of different bolus devices are found in U.S. Published Patent Application Nos. 2009/0187392 and 2007/0088194; and U.S. Pat. No. 6,059,733.

Acute outbreaks of disease continually threaten cattle, buffalo, sheep, pigs and other farm animals. Such outbreaks have caused substantial economic losses globally. For example, outbreaks of bovine spongiform encephalopathy (commonly known as mad cow disease) in the UK necessitated the slaughter of 3.3 million cattle with an estimated loss of over $7.2 B. A mad cow outbreak in the U.S. accounted for an annual loss of $2 B in beef exports. Similarly, a swine foot and mouth disease in Taiwan caused the destruction of over 3.8 million pigs and an estimated loss of $6.9 B.

Rapid and accurate diagnosis of disease in livestock is an important component of a comprehensive animal health program. Disease diagnosis in animals is often based on a combination of clinical signs and subsequent testing. Utilizing current methods, case definition is often subjective and confirmatory diagnostic test results are unavailable in real-time, if at all.

In an outbreak of a highly contagious disease, the ability to rapidly and accurately identify clinically ill animals is an important control point for mitigating disease transmission. Advances in electronics and wireless technologies have created bolus systems for monitoring discrete parameters such as temperature, heartbeat rate and respiration rate in livestock. The ability to remotely monitor animal wellness, condition and diagnose disease would provide a valuable surveillance method for the livestock industry.

Physiologic parameters in animals have been monitored as indications of well-being. The common parameters of temperature, heart rate and respiratory rate are often used to distinguish clinical illness. Most commonly, these are utilized as a reading at a single time point and not as a continuous data stream (or signal). Continuous monitoring of these physiologic variables would provide insight into the disease process and allow for early discrimination of clinical illness. A system that continuously samples physiologic parameters in animals and uses these samples to diagnose disease and condition, and then reports such disease remotely would be of great value.

Some proposed bolus systems are often complex, unreliable, and expensive. When each animal in a herd of thousands of animals is to be equipped with a bolus, each bolus cannot be unduly expensive.

BRIEF SUMMARY OF THE INVENTION

The invention features, in one example, a bolus which requires only a single sensor, typically an acoustic transducer, to measure physiological parameters such as temperature, the pH level of the subject's body fluid, the subject's heart rate, breathing rate, activity level, and the like. The bolus includes a chamber which admits body fluid therein in order to determine the temperature and pH level of the fluid and thus the subject. In various embodiments, the bolus includes its own power storage and charging circuit and a data transmission subsystem which includes a means for uniquely identifying the subject. A data processing subsystem within the bolus is capable of conducting on-board diagnosis of the subject and may include the ability to receive commands and data from an external source.

The subject invention, however, in other embodiments, need not achieve all these objectives and the claims hereof should not be limited to structures or methods capable of achieving these objectives.

The invention features, in one example, a bolus for insertion in a body fluid. One bolus includes a housing, a chamber in the housing admitting body fluid therein, and a transducer in the housing. The transducer provides a signal through the body fluid for measuring the pH level and/or temperature of the body fluid. The transducer also generates a signal in response to vibrations for detecting one or more physiological parameters.

One or more layers may be disposed between the transducer and the chamber to reduce interface reflections. The chamber may also include a high impedance material spaced from the transducer. In one version, a medium is disposed adjacent the transducer for measuring temperature.

One preferred bolus further includes a control subsystem configured to activate the transducer to provide a signal through the body fluid and to receive a signal generated by the transducer in response to vibrations. A power source in the housing powers the control subsystem. In one embodiment, the charging circuit is responsive to a voltage generated by the transducer in response to vibrations received by the transducer and the charging circuit supplies this voltage to the power source.

One preferred bolus further includes a data processing subsystem responsive to the control subsystem for analyzing signals to make a diagnosis. A transceiver in the housing transmits the diagnosis data and a memory stores diagnosis data.

In one example, the bolus comprises a chamber admitting fluid therein, a sensor providing a signal through the fluid for measuring the pH level and/or temperature of the fluid, the sensor generating a signal in response to vibrations for detecting one or more physiological parameters, a control subsystem configured to activate the sensor to provide a signal through said fluid and to receive a signal generated by the sensor in response to said vibrations, a data processing subsystem responsive to the control subsystem for analyzing the signals to make a diagnosis, and a transceiver in the housing for transmitting diagnosis data.

The invention also features a method of determining the health of a subject. One preferred method comprises inserting a bolus into the subject. The bolus includes a transducer and a chamber admitting fluid therein from the subject. The transducer is actuated to provide a signal through the fluid which is analyzed to measure the pH level and/or the temperature of the fluid. Also, signals generated by the transducer in response to vibrations are analyzed to detect one or more physiological parameters. The signals are analyzed to make a diagnosis which can then be transmitted to a receiver, such as a satellite or base station.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIGS. 22A-22B axe signals showing how a bowel movement can be ascertained in accordance with the invention;

FIGS. 23A-23B are signals showing how walking behavior can be ascertained in accordance with the invention;

FIGS. 24A-24B are graphs showing how signals can be used to ascertain drinking behavior in accordance with the invention;

DETAILED DESCRIPTION OF THE INVENTION

Figure 1:
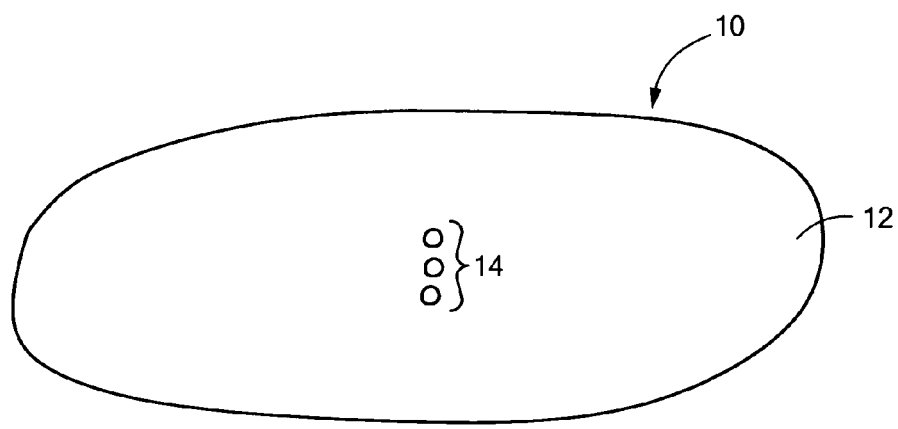
FIG. 1 is a highly schematic view showing an example of a bolus in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows an example of bolus 10 in accordance with the invention typically placed inside a subject, e.g., the reticulum of an animal, (e.g., a cow) to evaluate the health of the animal. Bolus 10 typically includes an outer housing 12 including one or more ports 14 opening into chamber 16, FIG. 2 allowing body (e.g., stomach) fluid to enter chamber 16.

Transducer 18 (e.g., a polycrystalline, single crystal, polymer, composite or piezoelectric element) within housing 12 is adjacent chamber 16 and transmits an acoustic signal as shown at 20a when energized to travel through the fluid in chamber 16 for measuring the pH level and/or temperature of the fluid in chamber 16.

In a passive mode, vibrations caused by breathing, motion, heartbeats, vocalizations, and the like are received as generally shown at 20b at transducer 18 and cause it to generate a signal indicative of these physiological parameters.

Also, in one specific design, transducer 18, in an active mode when energized, produces a signal 20c through medium 22 (e.g., a polymeric material) for measuring the temperature of medium 22 which is the same as or close to the temperature of the fluid in chamber 16 and the temperature of the subject. Medium 22 in one version may be disposed on the opposite side of the transducer 18 as well.

Optionally, transducer 18 also generates, in an active mode, an acoustic signal as shown at 20d when transducer 18 is energized to measure other physiological parameters such as body fat content. Thus, in one preferred embodiment, only one sensor is required to determine a number of physiological parameters.

Bolus 10 also typically includes one or more one quarter wave acoustic impedance matching layers 22a-d designed to reduce interface reflections. High acoustic impedance layers (>acoustic impedance of the fluid) 24a and 24b are also provided. Wall 12 can also be constructed of a high acoustic impedance material such as a metal with a protective (e.g., Teflon) outer coating.

In the example shown, bolus 10 also includes electronic section 30 including, for example, control circuitry which generates a signal to activate transducer 18 in the active mode (to, for example, provide signals 20a, 20c, and 20d) and which is responsive to and detects signals generated by transducer 18 in the passive mode. Such signals may include vibration signal 20b (indicative of movement, breathing, heart rate, and the like), the reflection of signal 20a off layer 24a, and/or the reflection of signal 20c off layer 24b, and/or the reflection of signal 20d off body tissue.

Electronic section 30 may also include a data processing subsystem responsive to the control circuitry for processing data (such as comparing measured responses to a stored template) derived from the various signals. Memory may also be provided to store this data and condition and disease templates as well as a unique identifier (e.g. serial number). Receiver/transmitter/antenna section 32 is used to transmit this data and/or the condition or disease identified, and typically the unique identifier outside of the bolus typically using RF frequencies and can also function to receive commands and data to modify the operation of the device.

Charging circuitry 34 includes a power source such as a battery or capacitor to provide power to transceiver 32 and the electronic section 30. In one preferred embodiment, the charging circuitry is responsive to voltages generated by transducer 18 and these voltages are used to charge an energy storage device such as a battery, capacitor or a hybrid system of these or similar devices. Voltages are generated by transducer 18, for example, in the passive mode, in response to vibrations (see signal 20b). The result is a bolus with an energy harvesting subsystem.

The temperature of the subject can be determined several ways. In one example, acoustic signal 20a emanating from transducer 18 through fluid 16 and reflecting off surface 24 returns to transducer 18 at different times and with different amplitudes depending on the pH level and the temperature of fluid 16. To determine the temperature of fluid 16 and thus the subject, the pH level can be calculated from the change in amplitude or assumed to be a certain value. The temperature of the fluid can thus be calculated from the different times of flight.

Alternatively, signal 20c can be used. The time it takes signal 20c to transverse known medium 22 sealed inside the bolus, reflect off wall 24b, and return to transducer 18 is indicative of the temperature of medium 22 and thus the subject.

The pH level of the fluid 16 inside the bolus can also be determined using a variety of methods. In one example, the temperature of the fluid 16 is determined via transducer signal 20c as described above. Then, the time it takes signal 20a to transverse fluid chamber 16, reflect off wall 24a, and return to transducer 18 is a function of the temperature and the pH level of the fluid in chamber 16. Since the temperature has already been determined, the pH level of the fluid can thus be ascertained. In another example, the magnitude of the return signal reflected off wall 24a can also be used to determine the pH level of the fluid.

Typically, electronics section 30 performs these calculations using a processor, for example. Once the pH level and temperature are calculated, the data processing subsystem determines the subject's health condition and stores data indicating the same in a memory for transmission by transceiver 32 to a satellite or base station.

Figure 2:
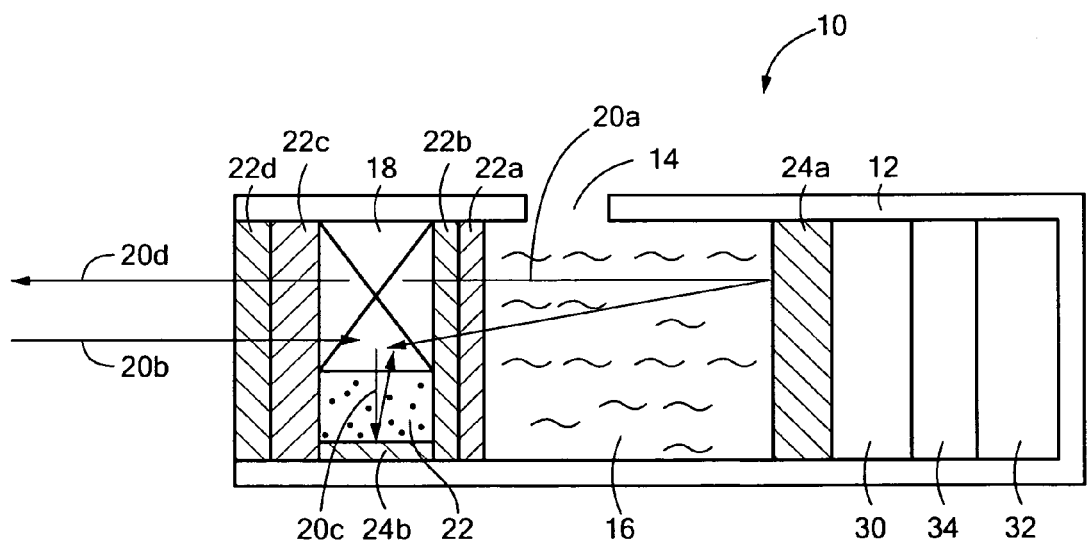
FIG. 2 is a schematic cross sectional view of the bolus shown in FIG. 1 showing the primary components thereof.
Figure 3:
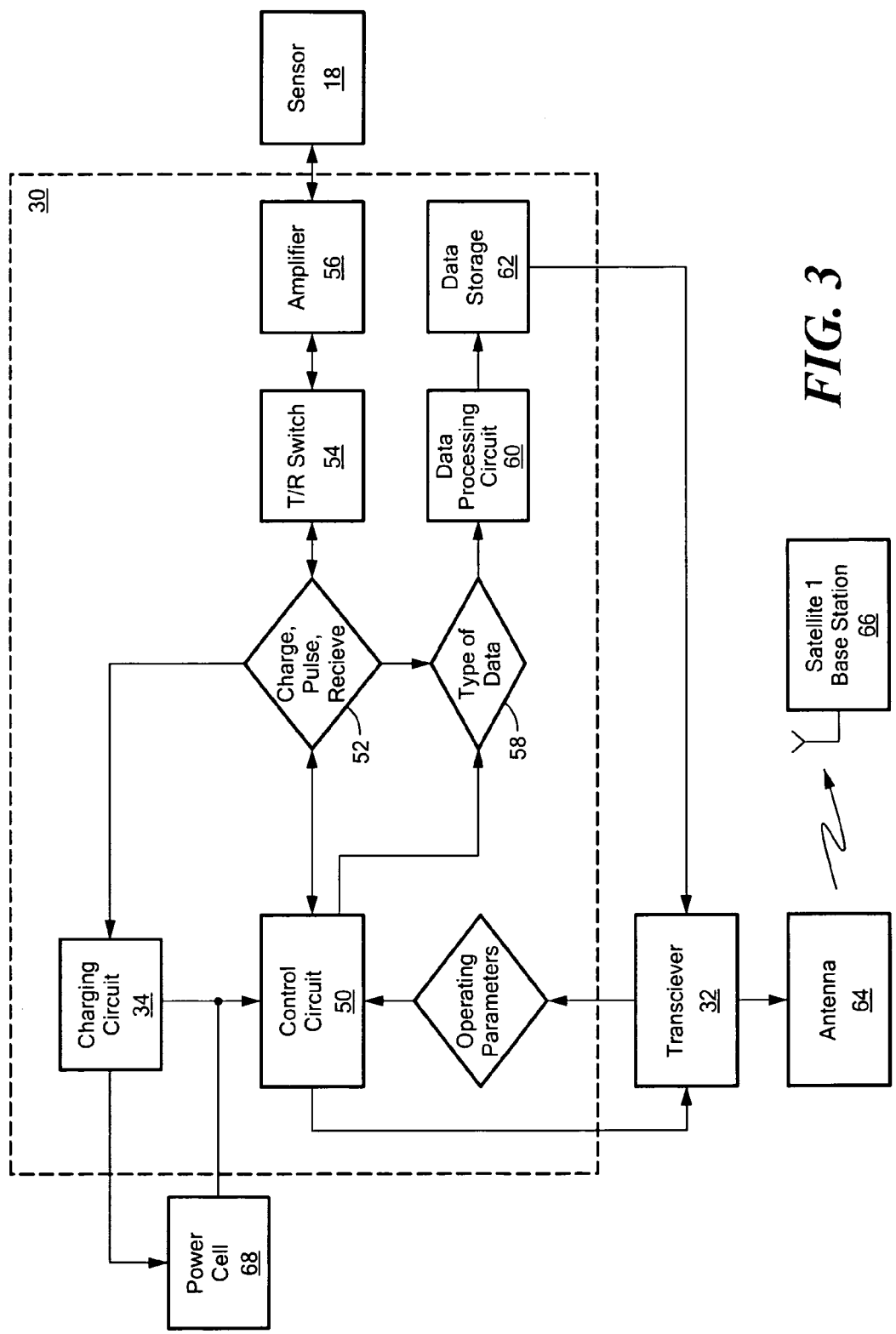
FIG. 3 is a block diagram also depicting the primary components associated with the bolus shown in FIGS. 1 and 2.

FIG. 3 shows one example of electronic section 30. Control circuit 50 provides a charge signal, a pulse signal, or it receives a signal from sensor 18 as shown at 52, for example, when transducer 18 is in a passive mode. A pulse signal activates switch 54, is amplified by amplifier 56, and activates transducer 18 in the active mode to emit an acoustic signal (see signals 20a, 20c, and 20d, FIG. 2).

A signal detected by transducer 18, FIG. 3 in the passive mode (for example, the reflection of signals 20a, 20c, or 20d or a vibration signal as shown at 20b) is amplified by amplifier 56 and passes through switch 54 to control circuit 50. Control circuit 50 determines, for example, the time it takes for signal 20a, FIG. 2, to traverse the fluid in chamber 16, reflect off wall 24a, again traverse the fluid in chamber 16 and activate the transducer 18; the time it takes signal 20c to traverse medium 22, reflect off wall 24b, and return to transducer 18; the signal characteristics of signal 20d after reflection off body tissue, and the signal characteristics of signal 20b received by the transducer in the passive mode.

Control circuit 50 then determines the type of data characterized by the signals as shown at 58. Data processing circuit 60 then processes the signals to determine temperature, pH level, heart rate, respiration rate, motion, vocalizations, body fat content, digestive activity and the like. Data processing circuit 60 also preferably determines, based on these physiological parameters, one or more possible conditions of the subject and stores data indicating the same in memory 62. This diagnosis data is then transmitted. The data processing circuit may also send the raw data for independent analysis.

Figure 4:
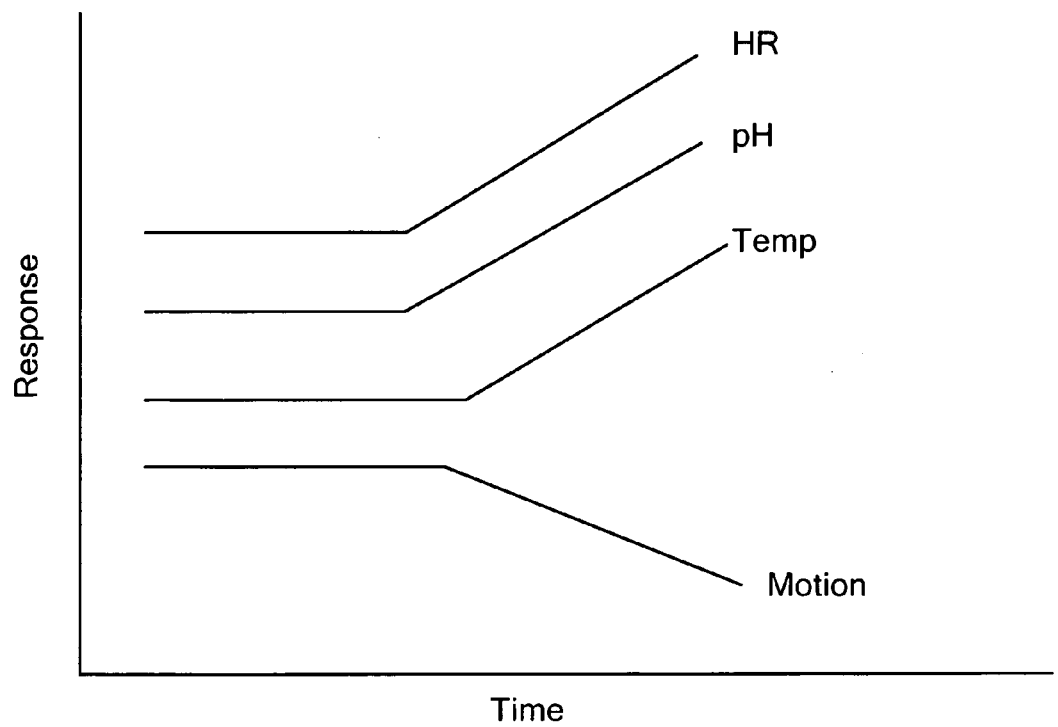
FIG. 4 is a graph showing how various physiological parameters can be monitored to provide an indication of a subject's health.

FIG. 4 depicts a simplistic example where subject's heart rate and pH level have all risen over a certain time period. But the subject's level of activity had decreased over the same time interval. Data processing circuit 60, FIG. 3 may thus store, in memory 62, a diagnosis that the subject has a certain medical condition.

Control circuit 50 then activates transceiver 32 to transmit this diagnosis via antenna 64. Control circuit 50 may be configured (e.g. programmed) to activate transceiver 32 to send transmissions only if certain medical conditions are diagnosed and even then only periodically. The receiver, such as the base or satellite station 66 then receives this condition or diagnosis information along with an identification of the bolus. Personnel monitoring satellite/base station 66 can then take the appropriate corrective action. The control circuit may also be capable of receiving information, via a transceiver allowing for updates to the templates and changes in the operational parameters.

In one example, a bolus is inserted into a subject already diagnosed with a certain disease. The subject's physiological data is monitored and stored. This process is then repeated for different diseases. The resulting data is then stored in the memory of each bolus. Then, for a given subject, a disease can be detected by comparing the stored data with the physiological data of that particular animal.

Also, when transducer 18 generates voltages because of the subject's motion, for example, control circuit 50 periodically routes this charge signal to charging circuit 34 for charging power cell (e.g., a battery) 68 which provides power for the various components of the bolus.

Typically, a microprocessor, application specific integrated circuit, controller, or the like is used to implement many of the functions of control circuit 50 and data processing circuit 60. Data may be reported in a specified format, a string of numbers corresponding to the subject's unique serialization, temperature, pH, and specific health condition or other form. The data may be encoded by the sensor to protect privacy and as required decoded at the receiving station to allow for the user to interpret the results.

Figure 5:
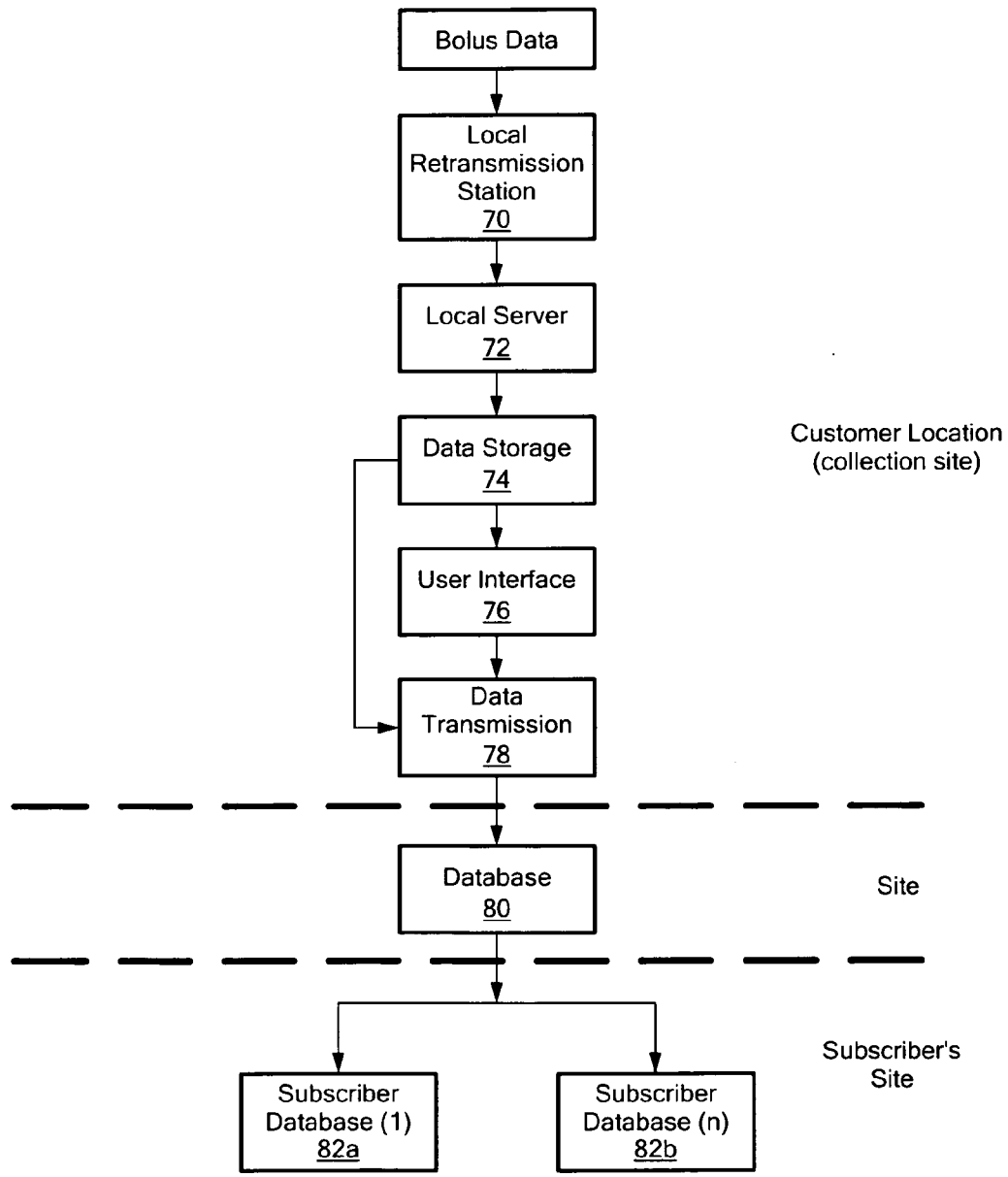
FIG. 5 is a block diagram showing how bolus data can be processed in accordance with the subject invention.

FIG. 5 shows how health data, with unique subject identification from a bolus is transmitted to local retransmission station 70 and local server 72 where the data is stored as shown at 74. The data may be viewed using user interface 76. This data may be further transmitted via the interne, for example, as shown at 78 to an end user's database 80. Various subscribers as shown at 82a and 82b may then view the database 80 and/or download bolus data to different databases as shown.

End users of the health data may include the U.S. Department of Agriculture, universities, pharmaceutical companies, and the like. Pay for subscription type services enable various users to subscribe to an end user's database 80.

The internal bolus system sensor that continuously samples animal parameters such as temperature, pH, acoustic and motion signatures and compares these samples to pre-stored sampled templates of parameters associated with known diseases can be used to distinguish clinical illness in real-time.

Figure 6:
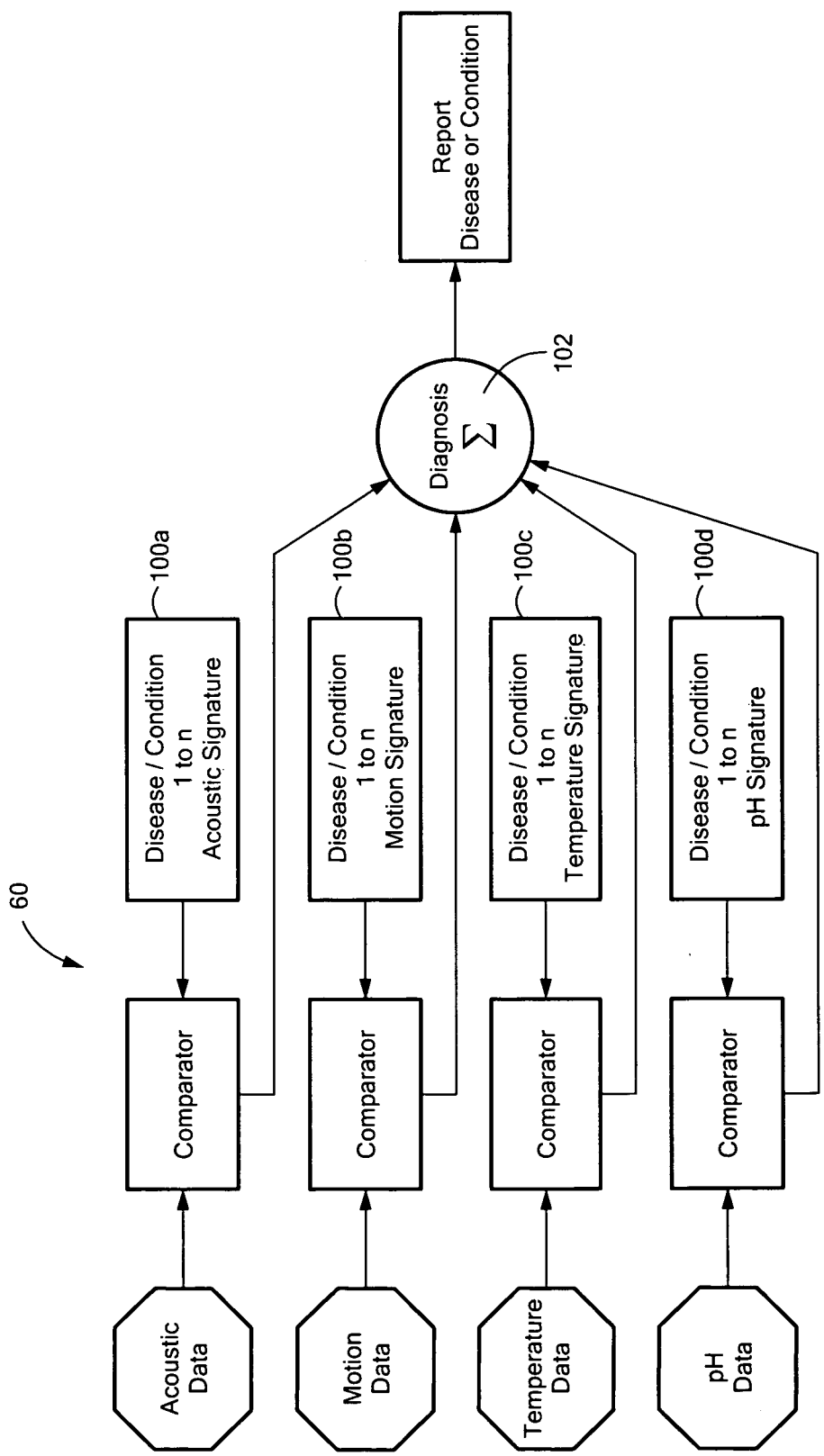
FIG. 6 is a block diagram showing the primary components associated with the data processing circuit shown in FIG. 3 configured to diagnose a disease in accordance with the invention and provide a unique identification.

The preferred bolus system data processing circuit continuously samples acoustic, motion, pH and temperature signatures of its host as shown in FIG. 6. The samples are digitized and compared to pre-stored sampled templates 100a-d of known diseases. If a matched is realized, the comparator output is automatically classified and matched with a disease or condition on file. The output is then summed into diagnosis summer 102. The summer automatically creates a three dimensional matrix for the parameters measured against n pre-stored disease templates to enhance the accuracy and early discrimination of clinical illness.

Figure 7:
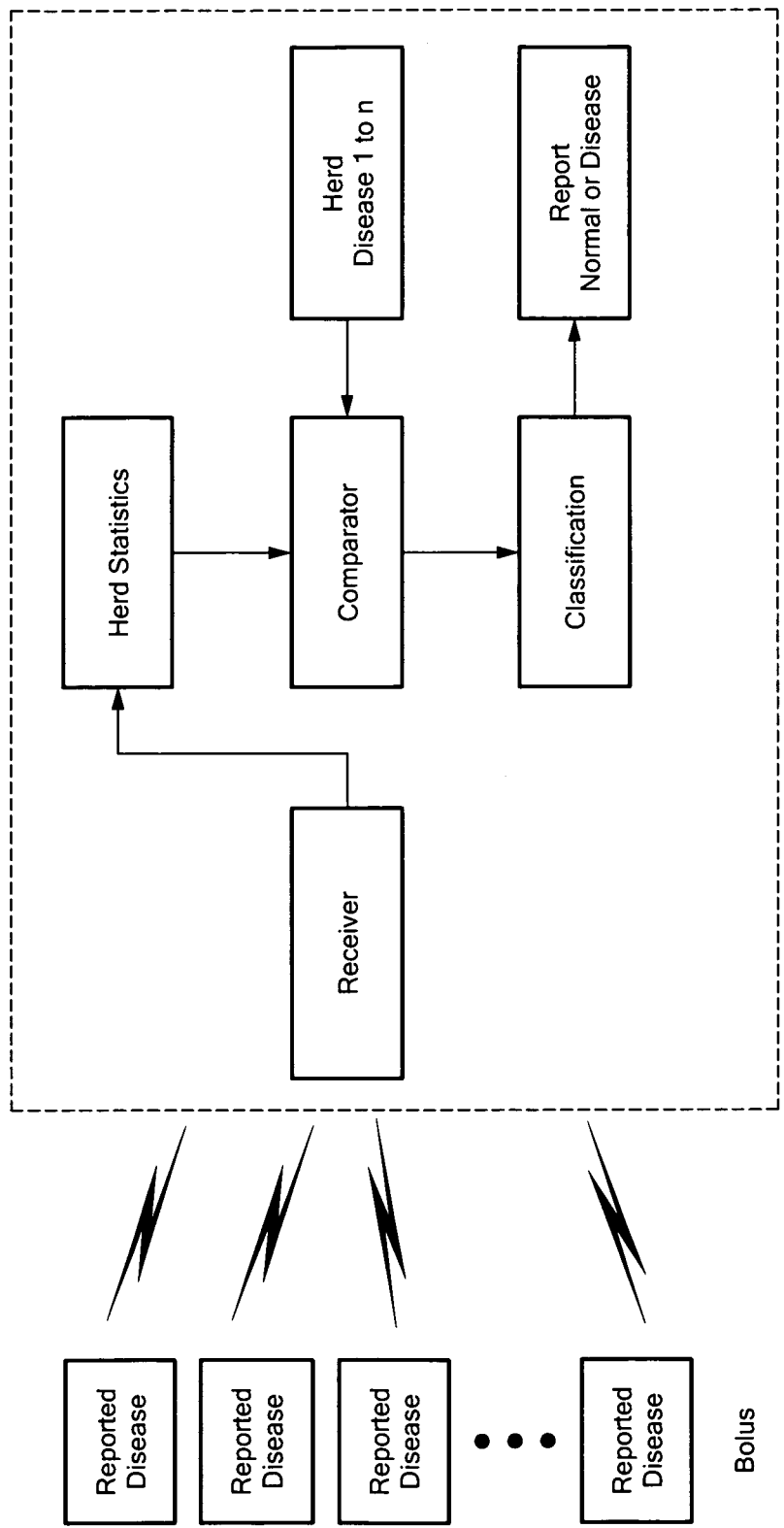
FIG. 7 is a block diagram showing the primary components associated with a remotely located processing device responsive to a number of bolus subsystems in accordance with the invention.

In addition to the individual diagnoses, discrimination of clinical illness is further enhanced when the entire herd's health is integrated and compared against known diseases and how such diseases spread through the herd. This integration is accomplished at a remotely located processing device and is illustrated in FIG. 7. For example, the temperature data from the entire herd is reported to the processing device. This measurement provides a baseline for comparison of the target animal. The device compares the data from the target animal to the median temperature of the herd. In normal conditions, the body temperature of the animal will vary as a function of the ambient temperature (i.e. on hot days the animal's core body temperature will be 1° to 2° higher than normal). The processing device will look at the entire herd's temperature and determine whether the target animal is likely running a fever. This process would be completed for each animal in the herd. Additional, the pH of an animal's digestive fluid is a function of the feed. Comparing individual changes to the herd will determine if a particular animal is behaving abnormally as compared to the rest of the population. Finally, while a particular behavior is often a sign of an illness, if the entire herd is exhibiting this behavior, it may suggest that there is a non-disease cause for this behavior. The ability to determine which responses (e.g., temperature, pH, etc.) are the result of illness and how many animals exhibit this, and when the symptoms are visible, will allow for the tracking of the spread of a disease, (e.g., over a period of five days), a specific number of animals develop a response that is different from the rest of the population.

Methods for collecting information that can be used to reduce operating costs have been identified by several feed lot operators as an additional key product performance requirement. Identifying changes in the density of the animal (lean-to-fat ratio) can also be accomplished by analyzing a received acoustic signal (see signal 20d, FIG. 2).

Transducer 18, FIG. 2 passively measures the acoustic signature of an animal and relays the response back to a data processing circuit 60, FIG. 3. The acoustic signature can be used to determine heart rate, respiratory behavior, and other health characteristics attributed to specific acoustic responses.

At predetermined intervals, transducer 18 is activated to determine time-of-flight information and/or reflection intensity. This data can be used to determine both temperature and pH. By placing the piezoelectric crystal in polymer baffle 22, FIG. 2, changes in the temperature of the baffle materials will change the damping of the two transverse modes (driven by changes in impedance originating from variation in stiffness of the baffle and the speed of sound). Moreover, by selecting a material that has a glass transition temperature in the range of the expected temperature swings of a health versus sick animal will maximize the information available by enhancing this phenomenon.

One preferred device utilizes energy harvesting techniques (such as energy from vibrations) to charge a storage device (battery, capacitor, etc.) which powers both the RF transceiver and pulses the transducer. Additionally, this device could be powered by a beta voltaic or similar device or a combination of both a battery and energy harvesting device. Included in the design are a T/R switch and electronics to store and transmit the relevant data as well as a means for a unique identification (e.g., RFID tag, microchip, etc.).

The output of the internal sensor 18 is typically represented as a function of time as x1(t). This signal is conditioned for analog-to-digital (A/D) conversion by passing it through low pass filter 120, shown in FIG. 8 with impulse response $h_1(t)$ to generate a filtered analog signal $x_2(t)$, which is equal to the convolution (*) of $x_1(t)$ with $h_1(t)$, and is mathematically expressed as:

$$x_2(t)=x_1(t)*h_1(t)=\int x_1(\tau)h_1(t-\sigma)d\tau \quad (1)$$

Figure 9:
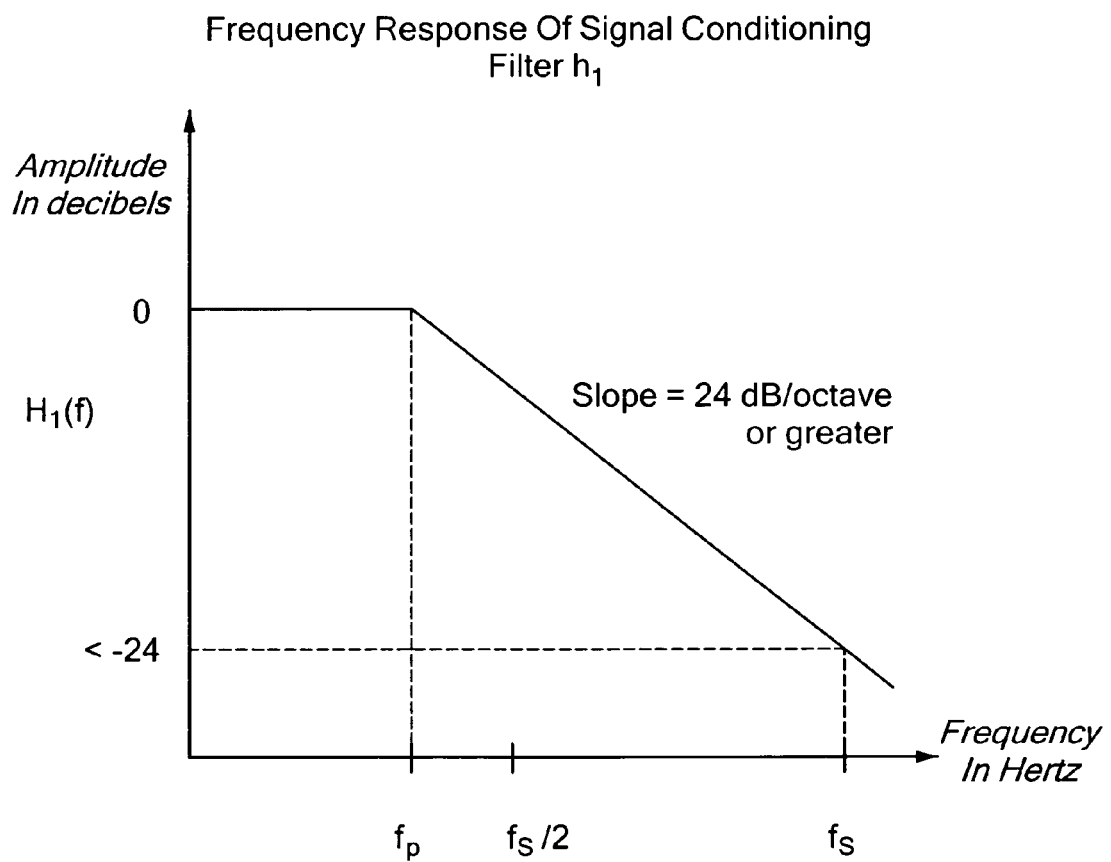
FIG. 9 is a graph showing the frequency response of the signal conditioning filter shown in FIG. 8.

Filter 120 is designed to pass all frequencies from 0 Hz to $f_P$ Hz, where $f_P$ is the highest frequency of interest ($f_P$ can a primary frequency or a harmonic of that frequency), which is less than or equal to half the sample rate, $f_S$, of A/D converter 122. Starting at the frequency $f_P$, the filter $h_1$ has a slope of at least 24 dB per octave, as illustrated in the design frequency response for the filter of FIG. 9.

Figure 10:
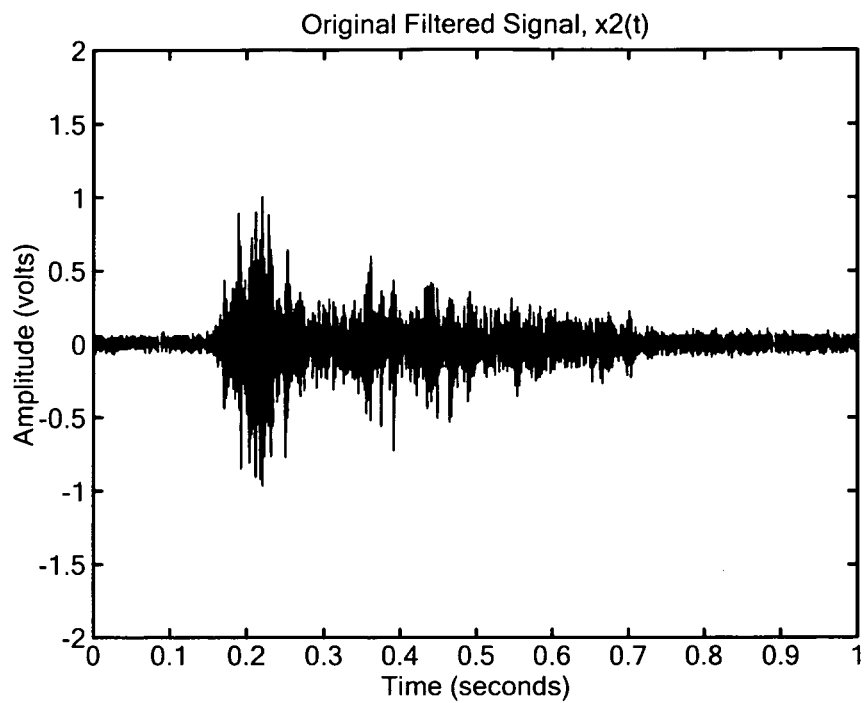
FIG. 10 is a graph showing the amplitude of a signal filtered by the signal conditioning filter shown in FIGS. 8 and 9.
Figure 11:
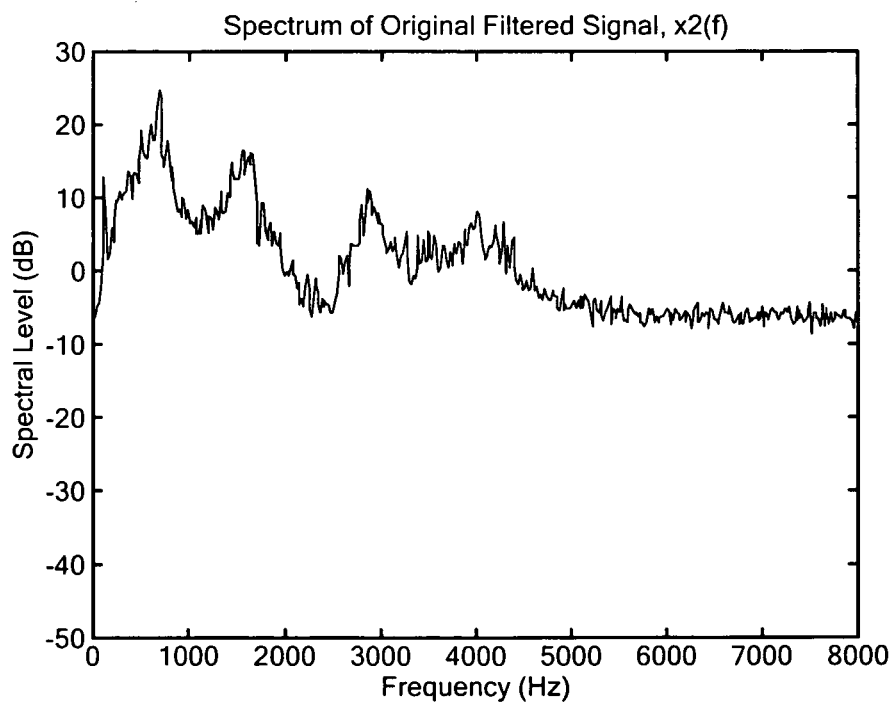
FIG. 11 is a graph showing the frequency spectrum of a signal filtered by the signal conditioning filter shown in FIG. 8.

An example of the analog filtered signal, $x_2$, is illustrated in FIG. 10, along with its spectrum as shown in FIG. 11. This example signal was generated for a passband of interest given by $f_P=7$ kHz.

Figure 8:
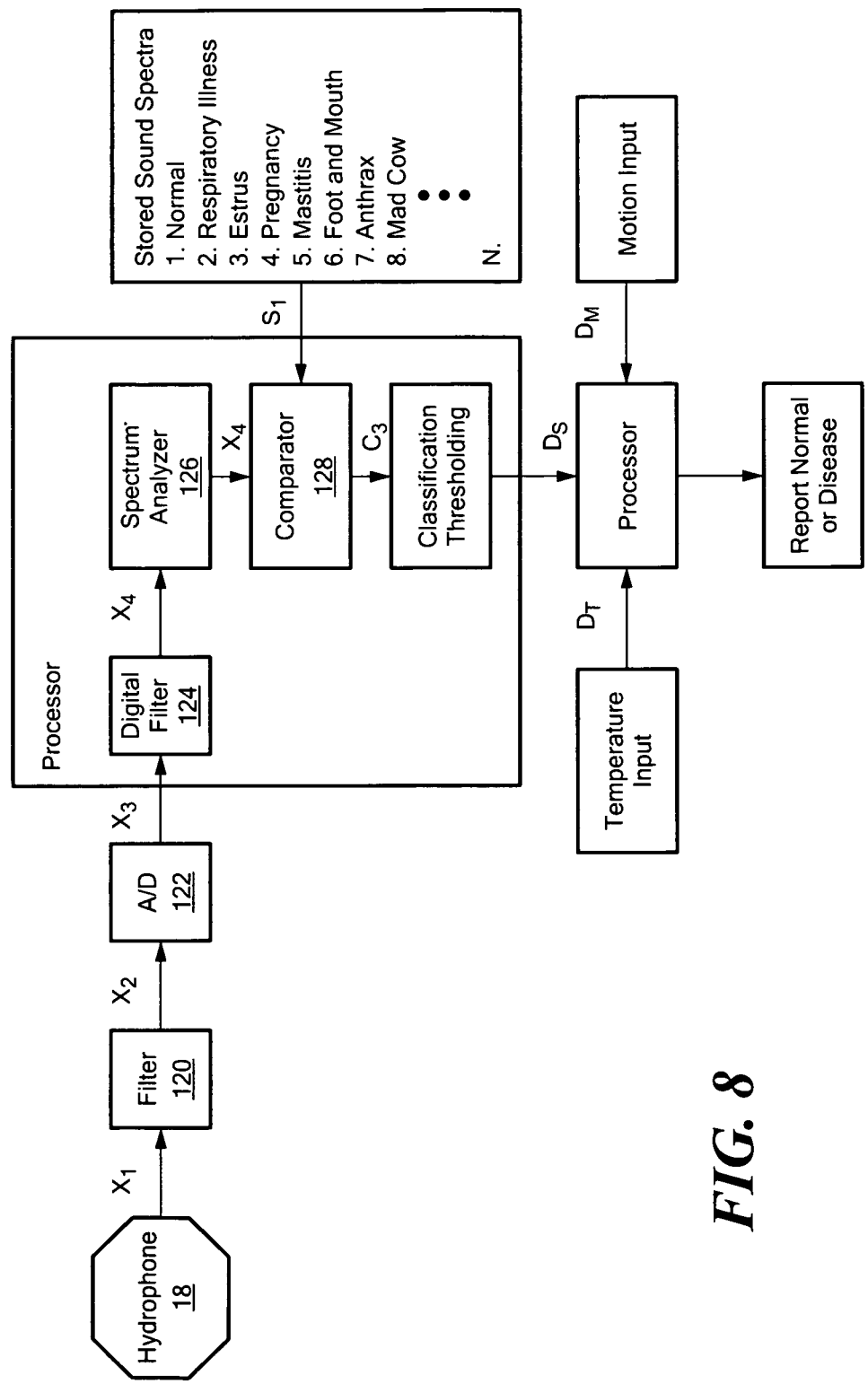
FIG. 8 is a block diagram showing the primary components associated with a data processing circuit in accordance with the invention configured to process signals generated by the transducer shown in FIG. 3.

The analog filtered signal conditioner output is then converted by converter 122, shown in FIG. 8 to a digitized signal, $x_3$, which can be expressed as:

$$x_3(nT)=x_2(t=nT), T=f_S/2 \quad (2)$$

Figure 12:
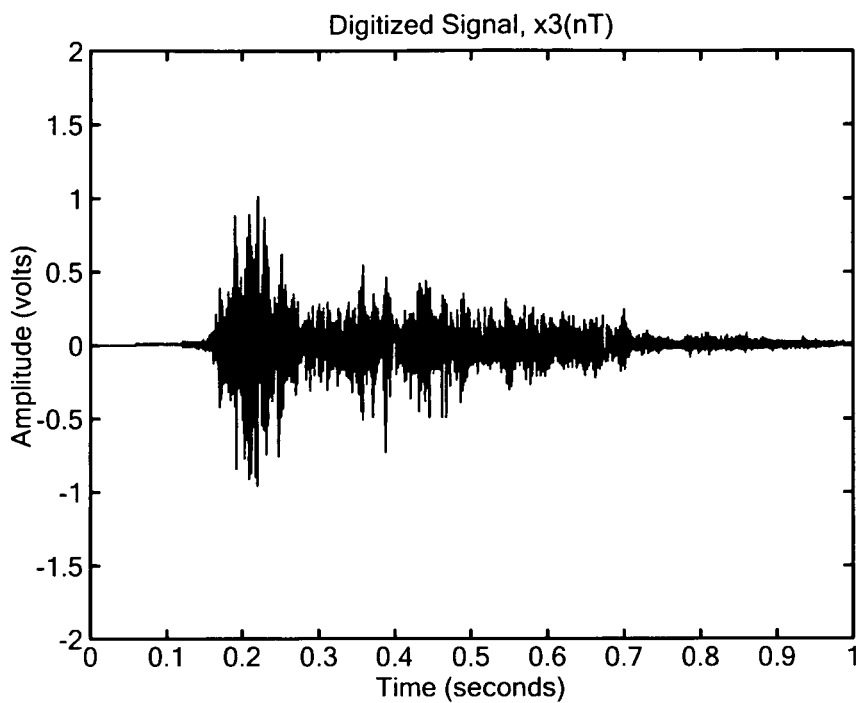
FIG. 12 is a graph showing the amplitude of a digitized signal output by the A/D converter shown in FIG. 8.
Figure 13:
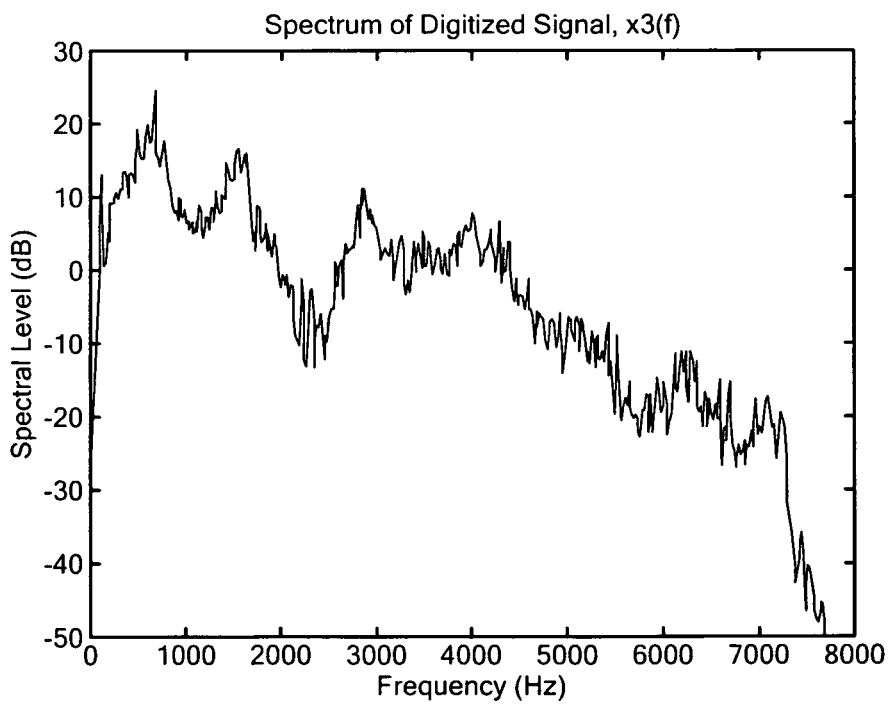
FIG. 13 is a graph showing the spectrum of a signal digitized by the A/D converter shown in FIG. 8.

Note that T is defined as the A/D sampling interval, and is equal to $f_S/2$. The A/D output signal, $x_3$, and associated spectrum for the example case is illustrated in FIGS. 12 and 13.

The digitized signal is then input to a low-pass Finite Impulse Response (FIR) filter 124 which includes M filter coefficients and is designed to pass only the frequencies of interest for classification, from 0 Hz to $f_C$ Hz. The digitally filtered output signal, $x_4$, is expressed as:

$$x_4(nT) = x_3(nT)*h_2(n) = \sum_{k=1}^{k=M} x_3([n-k+1]T)h_2(k) \quad (3)$$

where $h_2(k)$=FIR filter coefficients, k=1, 2, . . . N

Figure 14:
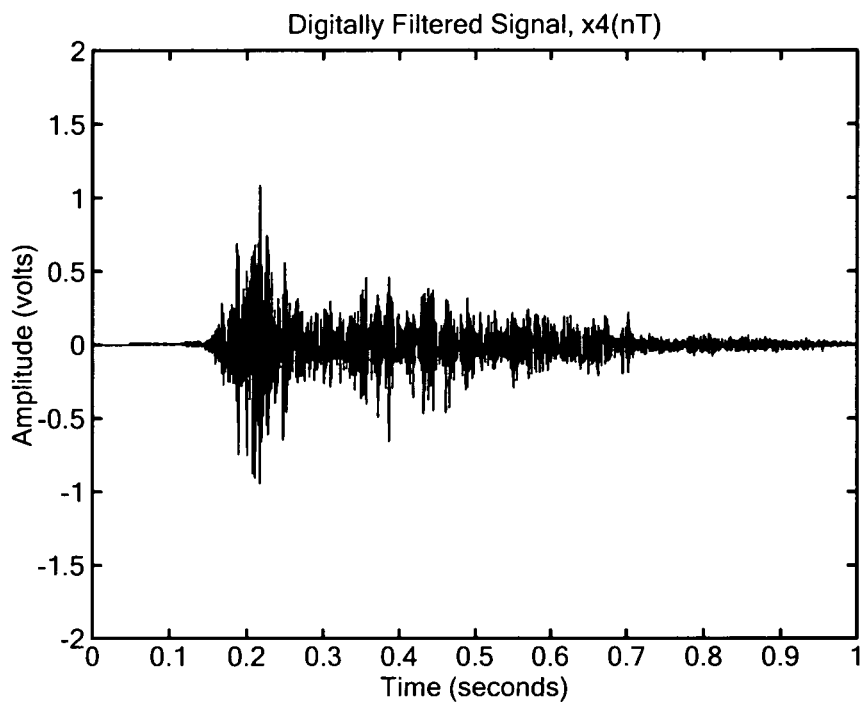
FIG. 14 is a graph showing an example of a signal after filtering by the digital filter shown in FIG. 8.

FIG. 14 illustrates the example low-pass filtered output digital signal, $x_4$, where the example filter was designed to pass classifier frequencies of interest from 0 Hz to $f_C=2$ kHz.

The digitally filtered signal is then analyzed by spectrum analyzer 126, by computing its Discrete Fourier Transform (DFT). This can be accomplished by first collecting a buffer of N sample points of the signal $x_4(nT)$ to define the buffered input signal, $x_m$ to the DFT as follows:

$$x_m=x_4(mT), m=0,1,2, \ldots N \quad (4)$$

Note that each new buffer of inputs to the DFT contains a percentage of overlapped points from the previous buffer, (e.g. ~25% of the data from the previous buffer). The DFT is then computed to generate N spectral estimation coefficients of the signal $x_4$ as follows:

$$X_4(k) = DFT\{x_4(nT)\} = \sum_{m=1}^{m=M} x_m e^{-2\pi i k m/N}, \quad (5)$$

$$k = 0, 1, 2, \ldots N_{DFT} - 1$$

Figure 15:
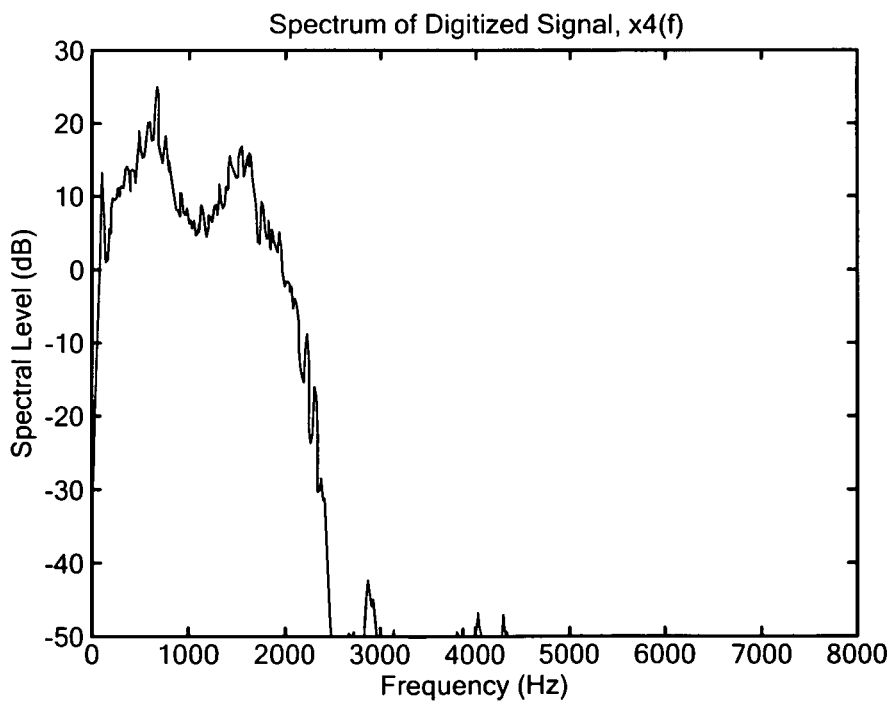
FIG. 15 is a graph showing an example of the frequency spectrum of a signal processed by the digital filter of FIG. 8.

In practice, a value of $N_{DFT}$ is used that is equal to a power of 2, so that the DFT can be implemented by a Fast Fourier Transform (FFT), which is much more computationally efficient than performing the DFT operation of equation (5). In addition, the value of $N_{DFT}$ is greater than some lower bound in order to obtain sufficient frequency resolution of the signal. FIG. 15 shows the DFT spectrum of the example signal, generated using a value of N=1024.

The output spectrum, $X_4(k)$ is then compared via comparator 128 to a set of N pre-stored representative sound spectrum templates ($S_i(k)$, i=1, 2, ... N) to classify the bolus sound as either normal or abnormal with an associated disease condition. This is done by correlating the magnitude spectrum of $X_4$ with that of each of the templates to generate a "sound classification measure". The measure for the $i^{th}$ stored template, $C_{Si}$, is the digital convolution of the monitored sound spectrum sample with that of the $i^{th}$ stored template, and is mathematically expressed as:

$$C_{Si}(k) = |X_4(k)| * |S_i(k)| = c \sum_{m=1}^{m=M} |X_4(m)||S_i(k+1-m)|, \quad (6)$$

$$k = 0, 1, 2, \ldots N_{DFT}/2 - 1$$

where c=normalization constant to insure that $0 \leq C_{Si}(k) \leq 1$

The overall sound classification measure, $C_S$, is the peak value of the individual measures as follows:

$$C_S = \max\{C_{Si}\}, i=1,2,3,\ldots N \quad (7)$$

This classification measure is compared to a minimum threshold value, $T_S$, to generate the sound classification decision, $D_S$, as follows:

$$D_S = C_S, \quad C_S \geq T_S \quad (8)$$
$$= 0, \quad \text{otherwise}$$

The sound classification decision measure is processed along with the classification decision measures from the temperature and motion signals, $D_T$ and $D_M$, respectively, to generate the final report of a normal or disease condition.

Speed of sound and density are influenced by the pH of a solution and its temperature. Additionally, the resonant frequency of a piezoelectric transducer is also a function of temperature. Using an active device to measure the speed of sound, characterize the amplitude of the receive signal and the frequency response of the transducer will allow us to simultaneously measure temperature and pH.

The relationship between speed of sound, density, and concentration (pH or salinity) of a fluid is discussed below.

A hydrophone can act as an accelerometer when allowed to move freely as in our application. For classifying illness or disease through abnormal motion, the transducer output is digitized, filtered and analyzed for its frequency content. The spectrum analyzer output is compared to pre-stored motion templates, until a match is found. The comparator output is automatically classified to detect normal and abnormal motions and matched with a condition on file. When a condition is determined, the output is summed into a diagnosis summary.

All data output by the transducer is in the time domain, and this needs to be processed from the time domain to the frequency domain. This is done by finding the Discrete Fourier Transform (DFT) by using a Fast Fourier Transform (FFT) as described in the sound sensor portion of this document in equations (4) and (5).

Figure 16:
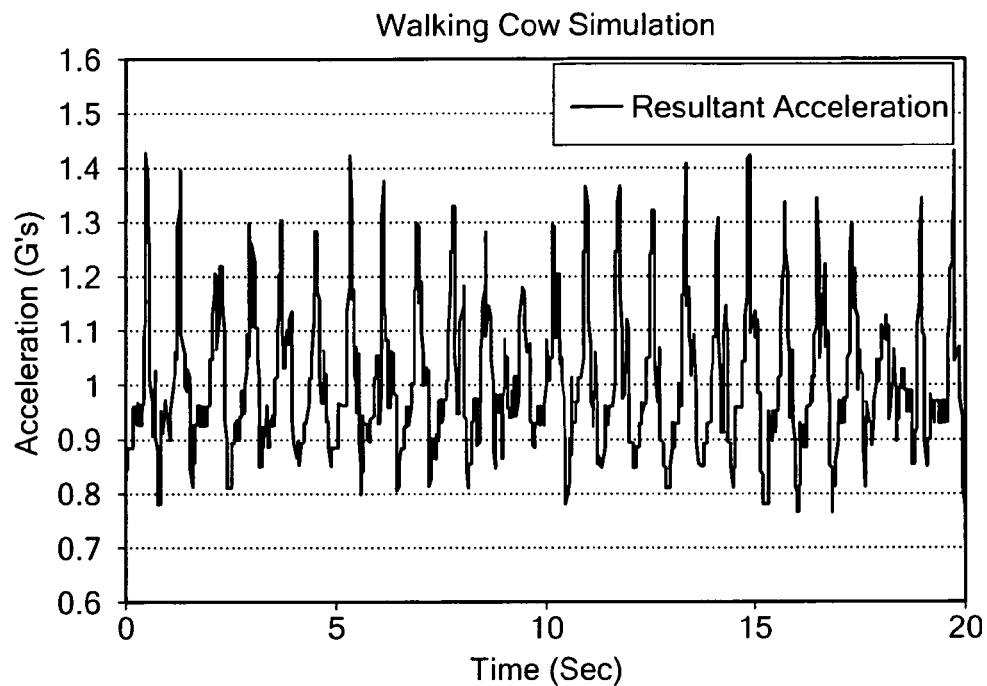
FIG. 16 is a graph showing the resultant simulated acceleration for a walking cow.
Figure 17:
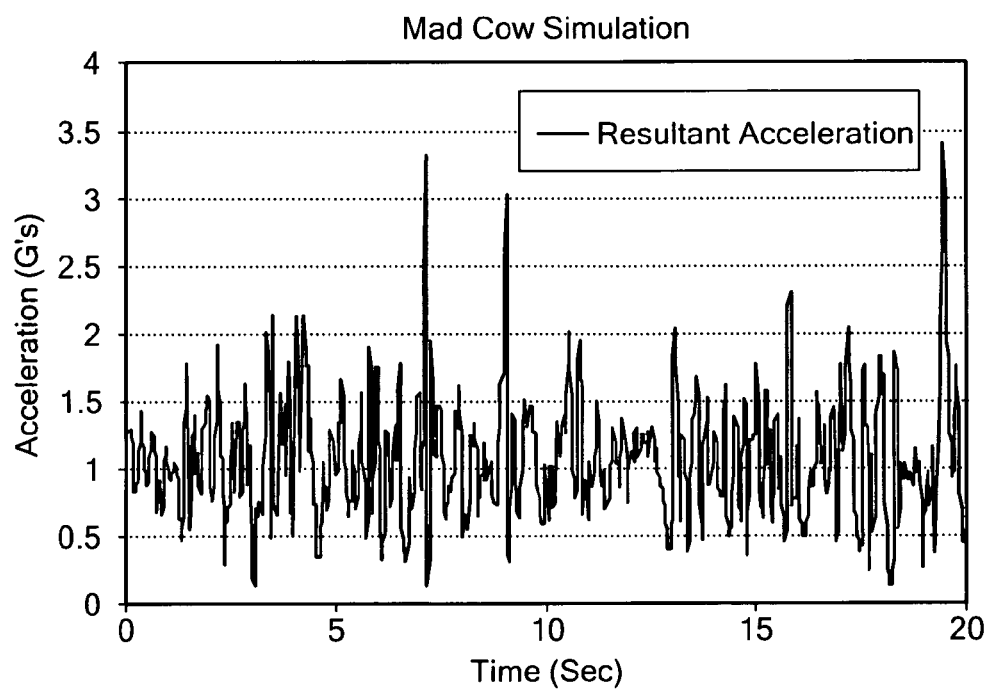
FIG. 17 is a graph showing resultant simulated acceleration for a cow suffering from mad cow disease.

An example of data that may be collected from a healthy cow as it walks is shown in FIG. 16. The analysis below is representative of what would be done with the hydrophone data. Another simulation was also performed to collect data that may be seen from a cow that has mad cow disease, shown in FIG. 17.

Figure 18:
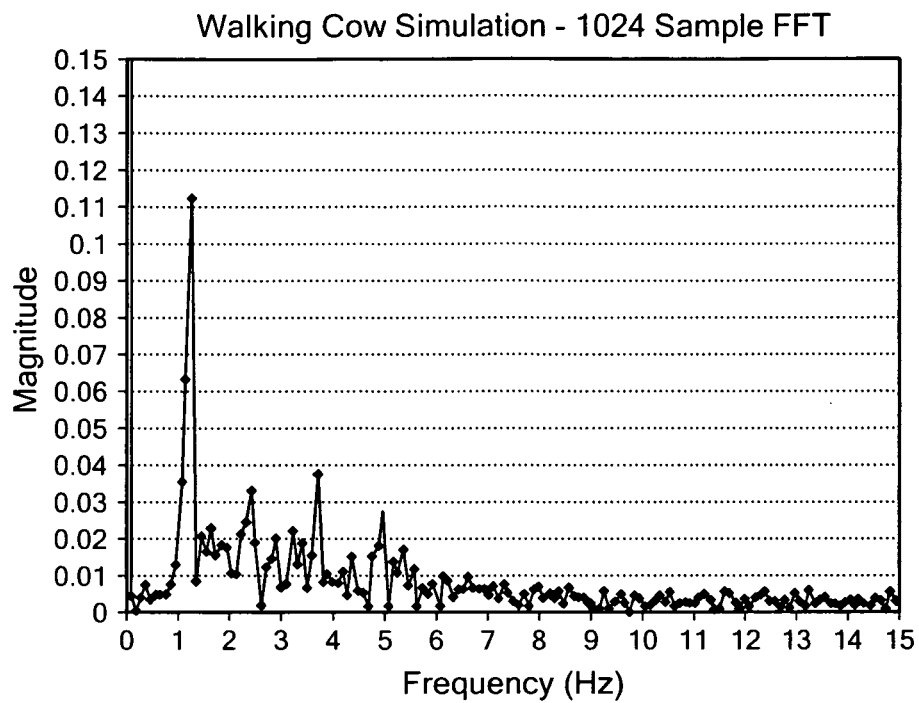
FIGS. 18-19 are graphs showing the frequency response of a walking cow simulation in accordance with the invention.
Figure 19:
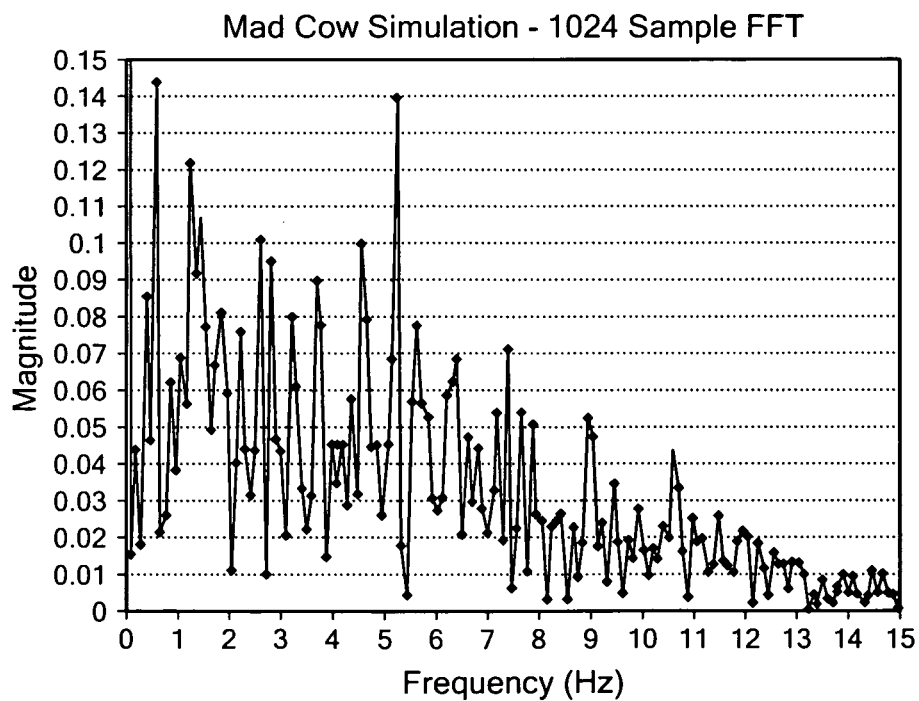

After completing a DFT on the signal resulting from an acceleration, the data is now in a frequency-magnitude form that allows for a comparison of the two sets of data. These new plots are shown in FIGS. 18-19. Using this data, the energies at specific frequencies can be compared against a database file of known illnesses and their frequency spectrums to determine a classification using the same process as in the sound sensor with equations (6) through (8). This will allow for proper healthy/diseased conclusions to be reached and the appropriate alerts can be sent out.

Data were collected after a transducer was inserted, at separate times, into a cow's rumen, via fistula. The signal from the transducer was recorded in .wav format using a portable digital recorder (in this case, a M-Audio Microtrak II). Specifications for the transducers is presented in Table 1:

TABLE 1

| Experimental hardware specifications | |
|---|---|
| | SQ26-08 |
| Frequency Range (±3 dB) [kHz] | 0.030 to 30 |
| Sensitivity [dB, re 1 V/μPa] | −194 |
| Preamplifier Gain [dB] | 25 |
| RMS Overload Acoustic Pressure [dB, re 1 μPa] | 154 |
| Maximum Operating Depth [m] | 100 |
| Operating Temperature Range [° C.] | −25 to 60 |
| Dimensions [mm] | 70 L × 32 dia. |
| Directionality | omnidirectional below 10 kHz |

The cow was monitored for an extended period of time while feeding, walking, and other typical cow activities using the hydrophone. In addition to recorded data veterinarians determined heart rate and respiration using a stethoscope.

Figure 20:
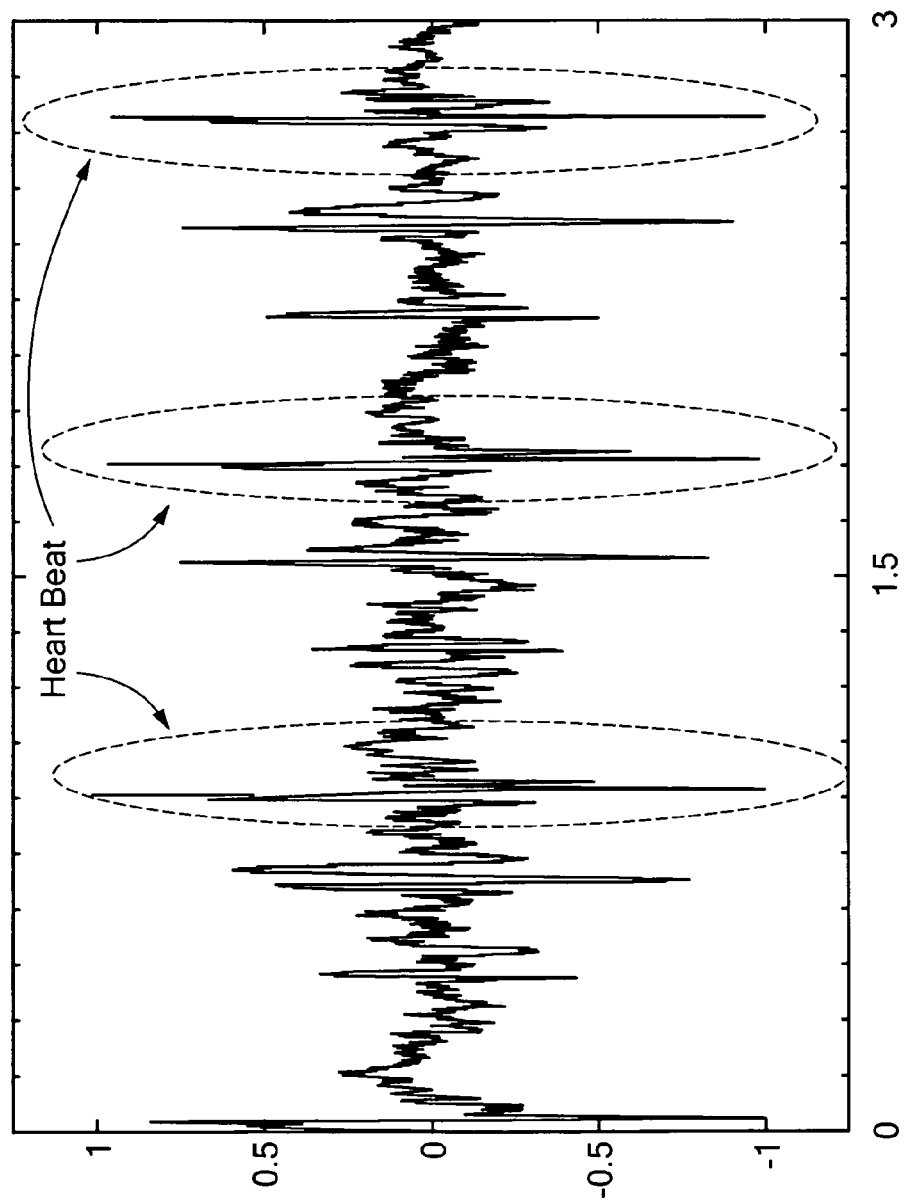
FIG. 20 is a graph showing how heart rate data can be ascertained in accordance the invention.
Figure 21B:
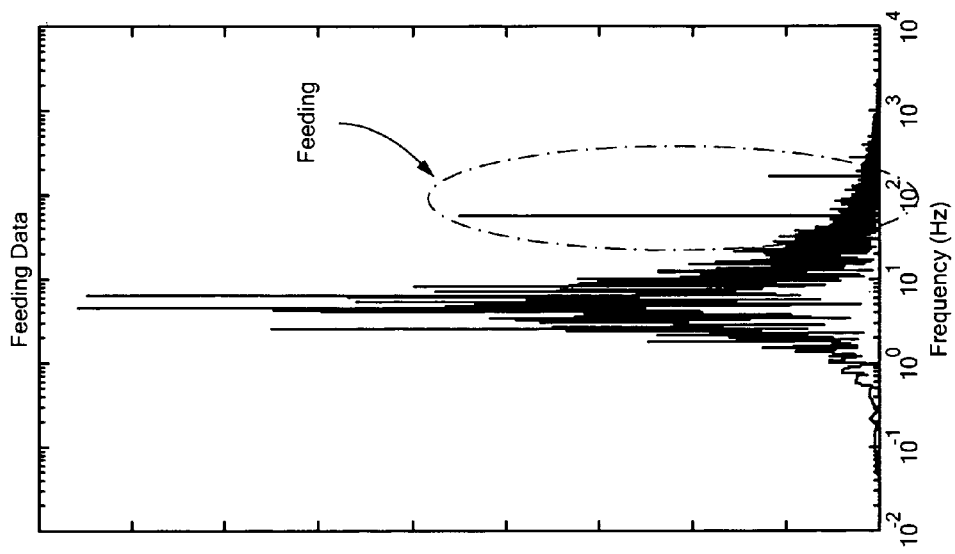
FIGS. 21A-21B are signals showing how feeding activity is ascertained in accordance with the invention.
Figure 21A:
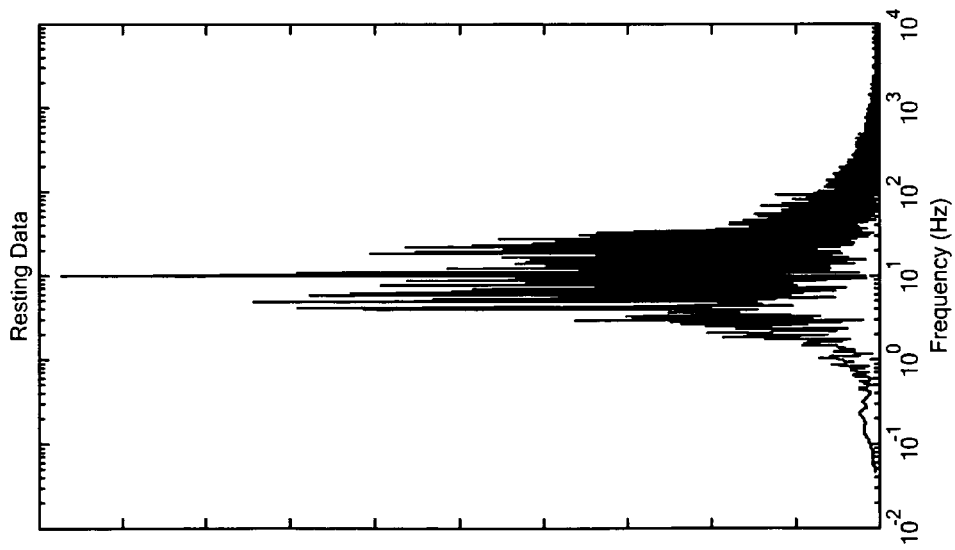
Figure 25B:
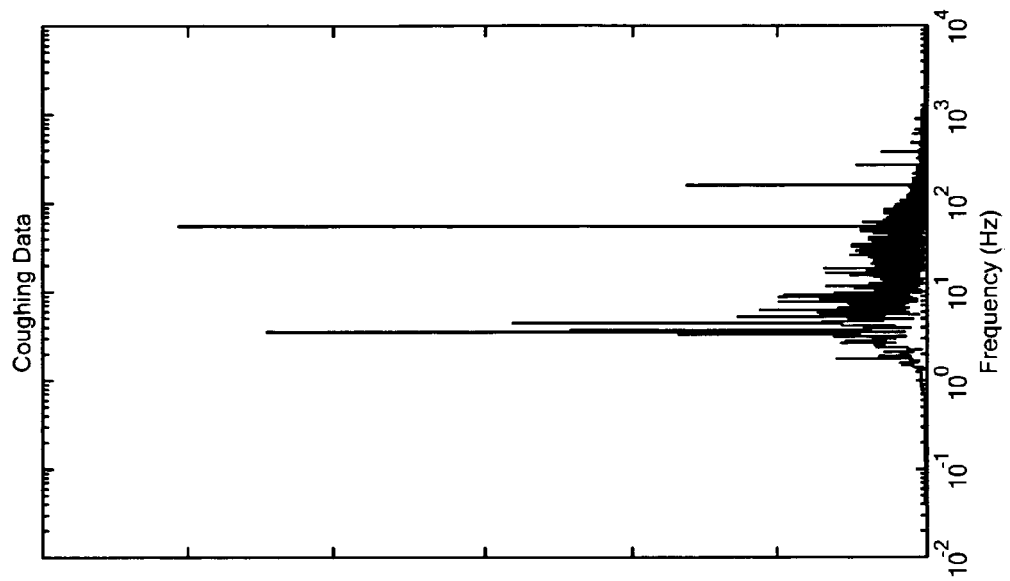
FIGS. 25A-25B are graphs showing how signals can be used to analyze coughing behavior in accordance with the invention.
Figure 25A:
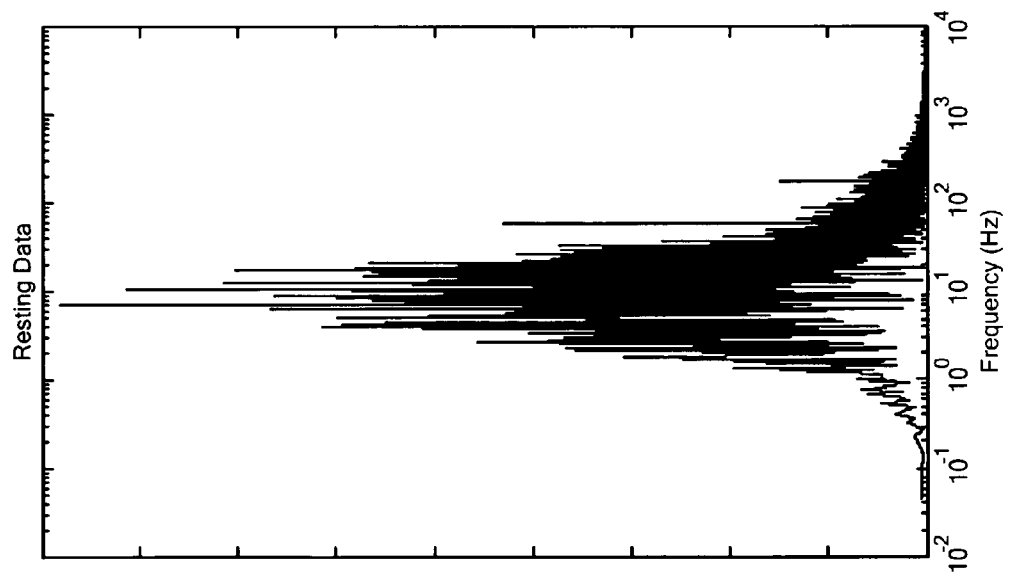

The .wav files were analyzed in the time and frequency domains at various time indices for known events. The estimated heart rate for the animal was one beat per second. Three seconds of data, captured with the SQ26-08 transducer is presented in FIG. 20. This data can be subtracted from the recorded data to eliminate the impact of the heart rate to analyze other events occurring during the same period.

FIGS. 21-25 show the results of analyzing the frequency response (via Fast Fourier Transform) during known activities and comparing them with resting data.

The following discussion addresses how temperature and pH can be decoupled from the time-of-flight data obtained from fluid chamber 16, shown in FIG. 2. The equation for time-of-flight consists of one equation and two unknowns—temperature and concentration (i.e. pH). Additionally, one of two methods of measurement will provide an independent measurement of either temperature or pH: 1) using lateral vibration modes to determine temperature only, and 2) using absorption to determine pH. Consequently, utilizing either of these methods in combination of the time-of-flight equation will provide a unique solution to the system of equations.

An acoustic point source radiating into a homogenous fluid at low frequencies is understood to be an omnidirectional source, i.e., its radiation pattern is symmetric as a function of angular location and the acoustic pressure at a fixed distance from the source in any direction is equal to any point located the same distance from the source but at a different angular position. If this source and fluid were to be surrounded by a surface whose acoustic impedance was substantially higher as compared to the fluid into which the source was radiating, then the radiated signal would be reflected upon normal impingement with the high impedance surface directly back to the source. If this surface was of uniform dimensions and the source was located concentrically in the surface i.e., all points of the reflecting surface are located equidistant from the source, the reflections in all directions would return to the source at the same time. The time-of-flight of the reflected wave would only be a function of the speed of sound in the material.

If the properties of the fluid were not homogeneous, as a function of angle, then the time-of-flight of the reflected wave, would be different. For example, if fluid 1 ($V_1$) was substantially slower than that of fluid 2 ($V_2$) the time for the reflected wave to return to the source would be longer for fluid 1, (i.e., $T_1 > T_2$).

The modulus of amorphous polymeric materials is known to vary as a function of temperature, among other things. Furthermore, this variation becomes increasingly significant in the vicinity of the glass-rubber transition region.

It has been widely reported that the modulus of a material is related to the speed of sound in the material. This has been demonstrated for metals, ceramics, and polymers. Consequently, factors that influence the modulus in a material can be expected to change the speed of sound in a material. Due to the temperature dependent nature of the modulus in polymeric materials, it is expected that the speed of sound will change as a function of temperature. If the operational temperature range is in the glass-rubber transition region, it is anticipated that small changes in temperature will result in large changes in the speed of sound.

The primary factors that influence modulus, assuming no chemical or physical decomposition, are temperature, pressure, and frequency. We do not expect pH (or other chemical changes, (such as UV degradation, etc.) to have short term effects on the modulus of the materials used in this sensor over the course of its operational life.

The temperature dependent response of the polymeric baffle material 22, FIG. 2 can be used to measure the temperature of the sensor.

The size of the resonator can be selected such that the difference in the time-of-flight of the wave emitted from a lateral deformation of the resonator can be resolved. Thus, variation in the speed of sound in the materials will be solely a function of changes in their modulus as a function of temperature. The baffle material can be selected such that it maximizes changes due to temperature.

There exist examples of methods to suppress these modes to improve transducer response, suggesting that these modes are strongly coupled to the performance of the device (see U.S. Pat. No. 5,948,993 incorporated herein by this reference which shows the various modes of operation of a simple piezoelectric disk). In standard industry nomenclature, the first ordinal indicates the poling direction and the second indicates the direction of deflection. For example, a device having the designation "33" indicates that the material is poled in the 3 direction and the deflection occurs in the 3 direction. In the case of a "31" device, the poling direction is in the 3 direction; however the deflection is in the 1 direction.

The proposed transducer would utilize both the 33 and 31 modes of operation. The 33 mode would be used to generate a pressure wave in the fluid chamber, while the 31 mode would be used to generate the effect discussed in above. Note that while the preferred embodiment is a polycrystalline material, piezoelectric composites exhibit a similar response, albeit for different reasons. The 15 mode (shear mode) may also be used depending on the construction of the device, and in particular the selection of the ¼ wave matching layers (typically two are used to form a graded material).

In the parlance of hydrophone design, suppression of the lateral modes results in an improvement in the "ring down" of the hydrophone. The amount of ringing determines the fidelity of the transducer with respect to resolving objects near to the face of the transducer. Typically, the ringing is "gated out" at a fixed time and the information is not used (i.e., investigators are looking for objects in front of the transducer and not the transducer itself). Changes in the ringing, as a result of the transducer design, can be correlated to changes in the temperature of the transducer. These changes should manifest themselves in a shift in the time domain due to changes in the speed of sound, as discussed, although it is likely that the magnitude of the ringing signal will also provide information on its temperature (i.e., temperature dependent absorption).

Consequently, temperature only data can be obtained in the proposed manner and this information can be used to resolve pH data from the time-of-flight and absorption measurements derived from the fluid chamber (from the two equations and two unknowns discussed above).

A study of sound absorption in the ocean demonstrated the correlation between changes in pH of seawater to changes in the sound absorption. Absorption of sound in fluids is a function of scattering and molecular relaxation. Phenomena that would change the density of a fluid, without contributing to the relaxations or scattering, are unlikely to impact absorption. In a homogenous fluid, with no particulates the absorption of sound is based solely on molecular relaxations. Consequently, polar materials, such as those that would increase the pH of a fluid will absorb sound through ionic relaxations by a mechanism in which soluble materials would promote the disassociation ions and thus an increase in pH and concomitant sound absorption.

Clearly, based on the phenomena stated above, in the fluid chamber the amplitude of the received signal and the time it takes to travel back to the transducer (furnishing two equations) will be a function of both pH and temperature (the two unknowns desired). Therefore, it is possible to determine both pH and temperature simultaneously.

The pH of a cow's digestion system is a function of the nature food it consumes and the microorganisms located in the system. Changes in the nature of the food result in a redistribution of the concentration of the microorganisms and thus a change in the pH of the digestion fluid. Specifically, certain types of microorganisms, which digest certain types of food, require different pH levels to function.

Due to the nature of beef production, animals sent to feed lots undergo a rapid change in the type of food they consume. Dairy cows for a variety of reasons may also undergo changes in food, typically related to the change in seasons and availability/quality of food. Based on the physiology of the specific animal, this may have no impact or result in either subacute or acute acidosis. Subacute acidosis tends to result in lower weight gain or reduced milk production, both of which impact the economics of the industry.

Acute acidosis can result in shock and/or death of the animal. There are no outward signs on illness, until the animal is found dead. If the animal does not perish, there are long term effects on the animal's health that result in loss of productivity (such as weight gain or milk production).

Figure 26:
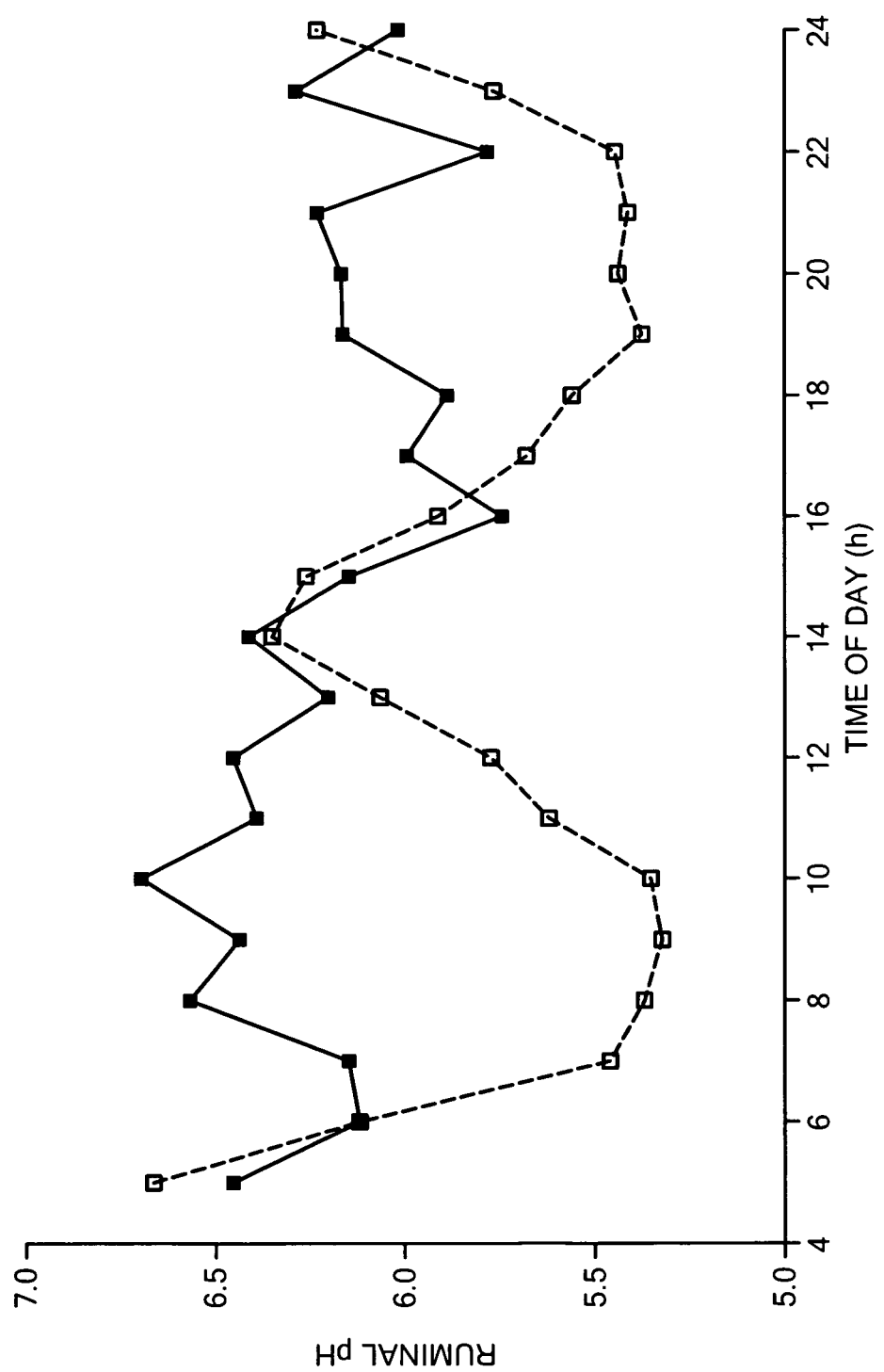
FIG. 26 is a graph showing the pH level of stomach fluid over known feeding cycles.

FIG. 26 indicates that the pH of a cow's stomach varies significantly as a function of feeding times. The data suggests that over the course of a day, depending on the feeding cycle, the pH of a cow's stomach returns to a nominal value at various points in the day after the completion of the digestion cycle.

Research has shown that most factors that influence the pH are linked to dietary intake. Consequently while the instantaneous pH may change due to these factors, the pH eventually returns to a baseline value. This indicates that measuring the pH over time will give a profile of the animal's digestive health, independent of the factors that may or may not influence stomach fluid density, independent of stomach pH.

The frequency of measurement can be directly linked to data from passive measurements on the frequency of feeding of the animal. For example, if the animal is on a 12 hour feeding cycle (as measured by the acoustic signature for feeding), the pH measurement could be measured approximately 8 hours after the feeding cycle every hour until the next feeding cycle. This data could be compared to the pH of the next measurement cycle.

The preferred device shown in FIG. 2 includes a polycrystalline piezoelectric element, a plurality of ¼ wave matching layers, a high acoustic impedance housing material (relative to the fluid being measured), an energy storage device that can be recharged by the piezoelectric element, control circuitry that regulates charging, pulse actuation, data collection periods, and the like, and a transmission device to send the data to a remote location for analysis.

The device will send a voltage signal, in the time domain, to a remote location for analysis. The analysis will consist of a time domain response characterization to determine pH and temperature, based on one or both of the methods discussed above. A frequency domain analysis will be conducted to determine motion, physiological responses, such as walking, drinking, respiration, etc. Both the time and frequency domain signals will be correlated to acceleration effects of the transducer.

The sensitivity of transducers may be impacted by acceleration effects and multiple methods have been developed to eliminate these effects. Large spikes in the "noise" due to acceleration can be used as a means to determine if the animal has moved and the intensity of the movement. This information, used alone or when combined with spectral responses will be correlated to motion of the animal (note that the spectral response could also be used alone to measure motion).

Based on the above discussion, the parameters such as pH, temperature, digestive cycle, motion, respiration, heart rate, belching, etc., can be used in the diagnosis of specific related diseases.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A bolus for insertion in a body fluid in a body cavity, the bolus comprising:
a housing;
a chamber in the housing configured to admit body fluid therein; and
a transducer in the housing, the transducer configured to:
induce a signal through the body fluid admitted into the chamber;
detect one or more parameters of the signal that has passed through the body fluid, the one or more parameters of the signal indicative of a pH level and/or temperature of the body fluid; and
detect ambient vibrations originating from outside the bolus, the vibrations indicative of one or more physiological parameters.

2. The bolus of claim 1, the bolus further comprising:
one or more layers between the transducer and the chamber, the one or more layers configured to reduce interface reflections.

3. The bolus of claim 1, the bolus further comprising:
a second chamber containing a medium, the second chamber adjacent to the transducer; and
wherein the transducer is further configured to induce a signal through the medium for measuring a temperature of the medium.

4. The bolus of claim 1, the bolus further comprising:
a control subsystem in the housing, the control subsystem configured to activate the transducer to induce the signal through the body fluid and the control subsystem configured to receive the one or more parameters of the signal and/or the ambient vibrations.

5. The bolus of claim 4, the bolus further comprising:
a power source in the housing, the power source configured to supply power to the control subsystem.

6. The bolus of claim 5, the bolus further comprising:
a charging circuit in the housing, the charging circuit configured to charge the power source.

7. The bolus of claim 6, wherein the charging circuit is responsive to a voltage generated by the transducer in response to vibrations received by the transducer, the charging circuit supplying the voltage to the power source.

8. The bolus of claim 4, the bolus further comprising:
a data processing subsystem responsive to the control subsystem, the data processing subsystem configured to analyze the one or more parameters and/or the ambient vibrations to produce diagnosis data.

9. The bolus of claim 1, the bolus further comprising:
a transmitter in the housing, the transmitter configured to transmit the diagnosis data.

10. The bolus of claim 8, the bolus further comprising:
a memory configured to store the diagnosis data and a subject identification information.

11. The bolus of claim 1, wherein the transducer is a bidirectional acoustic transducer.

12. The bolus of claim 1, wherein the one or more parameters of the signal are selected from the group consisting of a speed of the signal, a time delay of the signal, an amplitude of the signal, and a frequency response of the signal.

13. The bolus of claim 5, wherein the power source is an energy storage device.

14. A bolus for insertion in a fluid in a body cavity, the bolus comprising:
a chamber configured to admit fluid therein;
a transducer configured to:
  induce a signal through the fluid admitted into the chamber;
  detect one or more parameters of the signal that has passed through the fluid, the one or more parameters of the signal indicative of a pH level and/or temperature of the fluid; and
  detect ambient vibrations originating from outside the bolus, the vibrations indicative of one or more physiological parameters;
a control subsystem configured to activate the transducer to induce the signal through the fluid and the control subsystem configured to receive the one or more parameters of the signal and/or the ambient vibrations;
a data processing subsystem responsive to the control subsystem, the data processing subsystem configured to analyze the one or more parameters of the signal and/or the ambient vibrations to produce diagnosis data; and
a transmitter configured to transmit the diagnosis data.

15. The bolus of claim 14, the bolus further comprising:
one or more layers between the transducer and the chamber, the one or more layers configured to reduce interface reflections.

16. The bolus of claim 14, the bolus further comprising:
a second chamber containing a medium, the second chamber adjacent to the transducer; and
wherein the transducer is further configured to induce a signal through the medium for measuring a temperature of the medium.

17. The bolus of claim 14, the bolus further comprising:
a power source.

18. The bolus of claim 17, the bolus further comprising:
a charging circuit configured to charge the power source.

19. The bolus of claim 18, wherein the charging circuit is responsive to a voltage generated by the transducer, the charging circuit supplying the voltage to the power source.

20. The bolus of claim 14, the bolus further comprising:
a memory configured to store the diagnosis data and a subject identification information.

21. A method of determining the health of a subject, the method comprising:
inserting a bolus into the subject, the bolus comprising a transducer and a chamber admitting fluid therein from the subject;
actuating the transducer to induce a signal through the fluid admitted into the chamber;
detecting one or more parameters of the signal that has passed through the fluid, the one or more parameters of the signal detected by the transducer;
analyzing the one or more parameters of the signal detected by the transducer to measure a pH level and/or a temperature of the fluid;
detect ambient vibrations originating from outside the bolus, the vibrations the ambient vibrations detected by the transducer; and
analyzing the ambient vibrations to detect one or more physiological parameters.

22. The method of claim 21, the method further comprising:
producing diagnosis data based on the one or more parameters of the signal and/or the ambient vibrations.

23. The method of claim 22, the method further comprising:
transmitting the diagnosis data.

24. The method of claim 21, wherein the subject is selected from the group consisting of a cow, a buffalo, a sheep, and a pig.

25. The method of claim 24, wherein the subject is a cow.

26. A health monitoring system comprising a bolus for use inside of a subject and a base station for use outside of the subject, the system comprising:
the bolus for insertion in a body fluid in a body cavity of the subject, the bolus comprising:
  a housing;
  a chamber in the housing configured to admit body fluid therein;
  a transducer in the housing, the transducer configured to:
    induce a signal through the body fluid admitted into the chamber;
    detect one or more parameters of the signal that has passed through the body fluid, the one or more parameters of the signal indicative of a pH level and/or temperature of the body fluid; and
    detect ambient vibrations originating from outside the bolus, the vibrations indicative of one or more physiological parameters;
  a data processing subsystem in the housing, the data processing subsystem configured to analyze the one or more parameters and/or the ambient vibrations to produce diagnosis data; and
  a transmitter in the housing, the transmitter configured to transmit the diagnosis data; and
the base station, the base station comprising:
  a receiver configured to receive the diagnosis data.

27. The system of claim 26, wherein the base station further comprises memory configured to store the diagnosis data.

28. The system of claim 27, wherein the base station further comprises a user interface configured to display the diagnosis data.

* * * * *